United States Patent
Shiokawa et al.

[11] Patent Number: 5,104,890
[45] Date of Patent: Apr. 14, 1992

[54] BENZOPYRAN DERIVATIVES AND PROCESSES FOR PREPARATION THEREOF

[75] Inventors: Youichi Shiokawa, Ibaraki; Koichi Takimoto, Takarazuka; Kohei Takenaka, Sakai; Takeshi Kato, Ikeda, all of Japan

[73] Assignee: Fujisawa Pharmaceutical Company, Ltd., Osaka, Japan

[21] Appl. No.: 490,375

[22] Filed: Mar. 8, 1990

[30] Foreign Application Priority Data

| Mar. 28, 1989 | [GB] | United Kingdom | 8906950 |
| Apr. 24, 1989 | [GB] | United Kingdom | 8909278 |
| Nov. 28, 1989 | [GB] | United Kingdom | 8926822 |

[51] Int. Cl.$^5$ ............... C07D 417/04; C07D 311/68; A61K 31/425; A61K 31/35
[52] U.S. Cl. .................. 514/370; 514/385; 514/456; 548/193; 548/300; 549/404
[58] Field of Search ........... 548/193, 300; 549/404; 514/370, 385, 456

[56] References Cited

U.S. PATENT DOCUMENTS

| 4,849,432 | 7/1989 | Shiokawa | 548/193 |
| 5,028,711 | 7/1991 | Stenzel | 546/196 |

FOREIGN PATENT DOCUMENTS

| 344747 | 12/1989 | European Pat. Off. | 546/196 |
| 350805 | 1/1990 | European Pat. Off. | 546/196 |
| 294677 | 11/1989 | Japan | 546/196 |

OTHER PUBLICATIONS

Bergmann, J. Med. Chem 23 492 (1990).

Primary Examiner—Robert Gerstl
Attorney, Agent, or Firm—Oblon, Spivak, McClelland, Maier & Neustadt

[57] ABSTRACT

Benzopyrene derivatives effective for the treatment of hypertension have been prepared.

7 Claims, No Drawings

BENZOPYRAN DERIVATIVES AND PROCESSES FOR PREPARATION THEREOF

The present invention relates to novel benzopyran derivatives. More particularly, it relates to novel benzopyran derivatives which have pharmacological activities such as K+ channel activator action and the like, to processes for preparation thereof, to a pharmaceutical composition comprising the same and to a use of the same as a medicament.

Accordingly, one object of the present invention is to provide novel benzopyran derivatives, which are useful as K+ channel activator.

Another object of the present invention is to provide processes for preparation of said benzopyran derivatives.

A further object of the present invention is to provide a pharmaceutical composition comprising, as an active ingredient, said benzopyran derivatives.

Still further object of the present invention is to provide a use of said benzopyran derivatives as K+ channel activator, especially vasodilating agent, useful for treating or preventing K+ channel mediated diseases, for example, vascular disorders such as hypertension, angina pectoris, cardiac insufficiency, peripheral and cerebral vascular diseases, atherosclerosis, arrhythmia, and the like in human being or animals.

The benzopyran derivatives of the present invention are novel and can be represented by the formula (I):

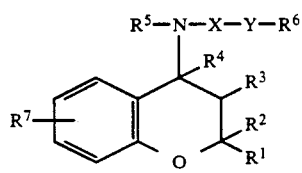

wherein
R¹ and R² are each lower alkyl,
R³ is hydroxy or acyloxy and R⁴ is hydrogen, or
R³ and R⁴ are linked together to form a bond,
R⁵ is hydrogen or lower alkyl and R⁶ is hydrogen, lower alkyl or aryl, or
R⁵ and R⁶ are linked together to form lower alkylene,
R⁷ is cyano, acyl, halogen, nitro or lower alkyl,
X is cyanoiminomethylene or sulfonyl, and
Y is single bond, thio, imino which may have lower alkyl,
provided that
i) when R⁷ is cyano, X is cyanoiminomethylene and Y is thio or imino which may have lower alkyl, then R⁵ is hydrogen or lower alkyl and R⁶ is aryl; and
ii) when R⁷ is cyano, R⁵ and R⁶ are linked together to form lower alkylene and X is sulfonyl, then Y is thio or imino which may have lower alkyl.

With regard to the compound (I) of the present invention, it is to be noted that there may be one or more stereoisomeric pairs due to the presence of one or more asymmetric carbon atom(s) or double bond and these isomers or a mixture thereof are included within a scope of the compound (I) of the present invention.

According to the present invention, the object compound (I) can be prepared by the following processes:

Process 1:

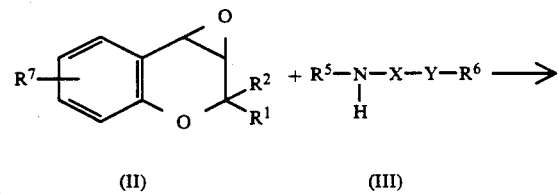

(II)      (III)
          or a salt thereof

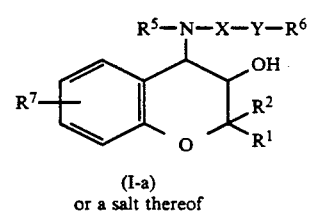

(I-a)
or a salt thereof

Process 2:

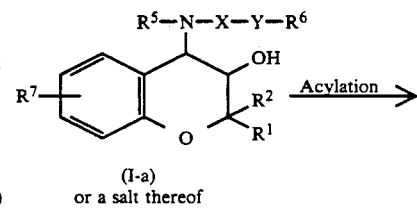

(I-a)
or a salt thereof

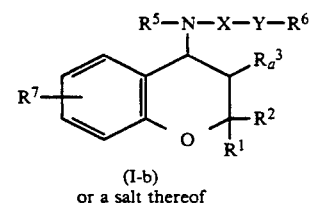

(I-b)
or a salt thereof

Process 3:

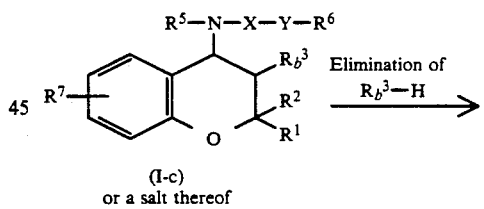

(I-c)
or a salt thereof

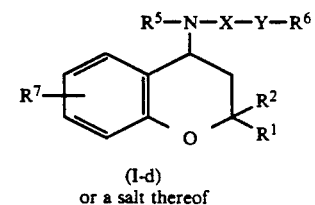

(I-d)
or a salt thereof

Process 4:

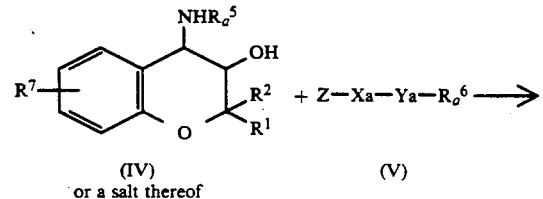

(IV)                    (V)
or a salt thereof

-continued

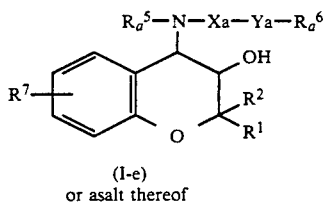

(I-e) or a salt thereof

Process 5:

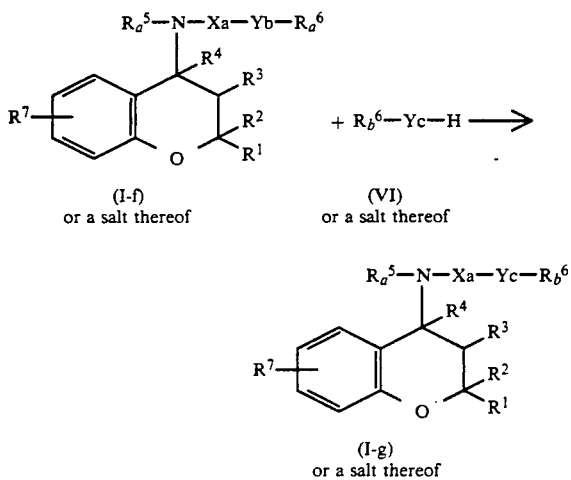

Process 6:

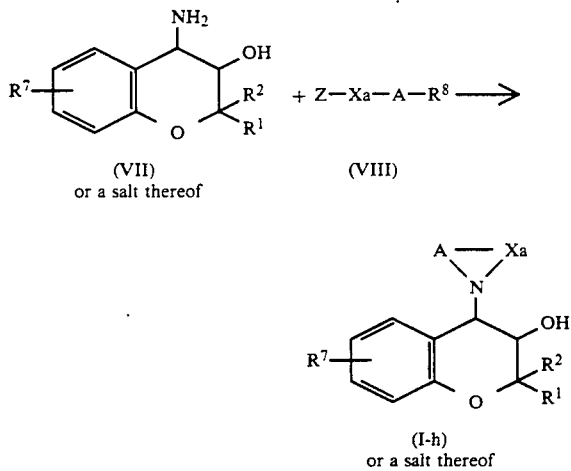

Process 7:

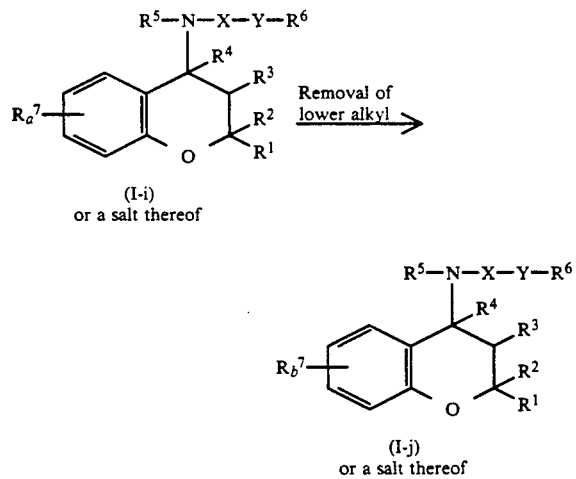

-continued wherein $R^1$, $R^2$, $R^3$, $R^4$, $R^5$, $R^6$, $R^7$, X and Y are each as defined above,
$R_a^3$ is acyloxy,
$R_b^3$ is hydroxy or acyloxy,
$R_a^5$ is hydrogen or lower alkyl,
$R_a^6$ and $R_b^6$ are each hydrogen, lower alkyl or aryl,
$R_a^7$ is lower alkoxycarbonyl,
$R_b^7$ is carboxy,
$R^8$ is acid residue,
Xa is cyanoiminomethylene,
Ya is single bond or thio,
Yb is thio,
Yc is imino which may have lower alkyl,
Z is leaving group, and
A is lower alkylene.

Suitable salts of the compound (I), (I-a), (I-b), (I-c), (I-d), (I-e), (I-f), (I-g), (I-h), (I-i), (I-j), (III), (IV), (VI) and (VII) are conventional non-toxic, pharmaceutically acceptable salts and may include a salt with a base or an acid addition salt such as a salt with an inorganic base, for example, an alkali metal salt (e.g. sodium salt, potassium salt, cesium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.), etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like.

In the above and subsequent descriptions of the present specification, suitable examples and illustrations of the various definitions which the present invention include within the scope thereof are explained in detail as follows.

The term "lower" is intended to mean 1 to 6 carbon atoms, preferably 1 to 4 carbon atoms, unless otherwise indicated.

Suitable "lower alkyl" may include straight or branched one, having 1 to 6 carbon atom(s), such as methyl, ethyl, propyl, isopropyl, butyl, t-butyl, pentyl, hexyl, or the like, in which the preferred one is methyl, ethyl or propyl.

Suitable "lower alkylene" and the lower alkylene moiety formed by linkage of $R^5$ and $R^6$ may include methylene, ethylene, propylene, trimethylene, tetramethylene, pentamethylene, hexamethylene, or the like, in which the preferred one is methylene, ethylene or trimethylene.

Suitable "acyl" and acyl moiety of "acyloxy" may include aliphatic, aromatic, araliphatic, heterocyclic and heterocyclic-aliphatic acyl derived from carboxylic, carbonic, carbamic and sulfonic acid, and the preferable example of said acyl moiety may be carboxy, lower alkanoyl (e.g. formyl, acetyl, propionyl, butyryl, pentanoyl, hexanoyl, etc.), lower alkylsulfonyl, (e.g. mesyl, ethylsulfonyl, propylsulfonyl, butylsulfonyl, hexylsulfonyl, etc.), N,N-di(lower)alkylsulfamoyl (e.g. dimethylsulfamoyl, diethylsulfamoyl, dipropylsulfamoyl, diisopropylsulfamoyl, dihexylsulfamoyl, etc.), lower alkoxycarbonyl (e.g. methoxycarbonyl, ethoxycarbonyl, propoxycarbonyl, etc.), and the like.

Suitable "halogen" means fluoro, chloro, bromo and iodo.

Suitable "leaving group" may include lower alkylthio (e.g. methylthio, ethylthio, etc.), and the like.

Suitable "aryl" may include phenyl, tolyl, xylyl, cumenyl, mesityl, naphthyl, and the like, preferably one having 6 to 10 carbon atoms, in which the preferred one is phenyl.

Suitable "acid residue" may include halogen as mentioned above, acyloxy (e.g. tosyloxy, mesyloxy, etc.) and the like.

Suitable "lower alkoxycarbonyl" may include methoxycarbonyl, ethoxycarbonyl, propoxycarbonyl, and the like.

The processes 1 to 7 for preparing the object compound (I) of the present invention are explained in detail in the following.

Process 1

The object compound (I-a) or a salt thereof can be prepared by reacting the compound (II) with the compound (III) or a salt thereof.

The present reaction is usually carried out in the presence of a base such as alkyl lithium (e.g. n-butyl lithium, etc.), alkali metal hydride (e.g. sodium hydride, potassium hydride, etc.), tri(lower)alkylanine (e.g. trimethylamine, triethylamine, etc.), pyridine or its derivative (e.g. picoline, lutidine, 4-dimethylaminopyridine, etc.), or the like, in case that the compound (III) is used in a free form.

The present reaction is usually carried out in a solvent such as dioxane, dimethyl sulfoxide, dimethylformamide, diethylformamide, dimethylacetamide, benzene, tetrahydrofuran, or any other solvent which does not adversely affect the reaction. In case that the base to be used in liquid, it can also be used as a solvent.

The reaction temperature is not critical and the reaction is usually carried out under cooling, at ambient temperature or under heating.

The object compound (I-a) can be used as a starting compound of the Process 2 mentioned hereinbelow with or without isolation.

Process 2

The object compound (I-b) or a salt thereof can be prepared by acylating the compound (I-a) or a salt thereof.

The acylating agent used in this reaction is a conventional one which is capable of introducing the acyl group as mentioned above into a hydroxy, and may preferably be lower alkanecarboxylic acid, lower alkanesulfonic acid, their acid anhydride, their acid halide, their activated ester, their acid amide, and the like.

In case that the acylating agent is used in a free acid form, the reaction is usually carried out in the presence of a conventional condensing agent such as carbodiimide compounds, and the like.

This reaction is preferably carried out in the presence of a base such as those given in the explanation of the Process 1 mentioned above.

This reaction is usually carried out in a solvent such as dimethylformamide, tetrahydrofuran, pyridine or any other solvent which does not adversely affect the reaction.

The reaction temperature is not critical, and the reaction can be carried out under cooling to warming.

Process 3

The object compound (I-d) or a salt thereof can be thereof to elimination reaction of the compound $R_b^3$—H.

The elimination reaction can usually be carried out by an inorganic base such as alkali metal hydride (e.g. sodium hydride, potassium hydride, etc.), or the like, and an organic base such as trialkylamine (e.g. trimethylamine, triethylamine, etc.), picoline, N-methylpyrrolidine, N-methylmorpholine, 1,5-diazabicyclo-[4.3.0]non-5-one, 1,4-diazabicyclo[2.2.2]octane, 1,5-diazabicyclo[5.4.0]undecene-5, 1,8-diazabicyclo[5.4.0]undec-7-ene or the like.

This reaction can be carried out in a conventional solvent which does not adversely affect the reaction such as those given in the explanation of Process 1.

The reaction temperature is not critical and the reaction is usually carried out under cooling, at ambient temperature or under heating.

Process 4

The object compound (I-e) or a salt thereof can be prepared by reacting the compound (IV) or a salt thereof with the compound (V).

This reaction is usually carried out in a solvent such as alcohol (e.g. methanol, ethanol, etc.), N,N-dimethylformamide, tetrahydrofuran, toluene: or any other solvent which does not adversely affect the reaction.

The reaction may be carried out in the presence of an inorganic or an organic base such as tri(lower)alkylamine (e.g. trimethylamine, triethylamine, etc.), pyridine or its derivative (e.g. picoline, lutidine, 4-dimethylaminopyridine, etc.), or the like. In case that the base to be used is liquid, it can also be used as a solvent.

The reaction temperature is not critical, and the reaction can be carried out under warming or heating.

Process 5

The object compound (I-g) or a salt thereof can be prepared by reacting the compound (I-f) or a salt thereof with the compound (VI) or a salt thereof.

The reaction may be carried out in the presence of an inorganic or an organic base such as tri(lower)alkylamine (e.g. trimethylamine, triethylamine, etc.), pyridine or its derivative (e.g. picoline, lutidine, 4-dimethylaminopyridine, etc.), or the like.

This reaction is usually carried out in a solvent such as alcohol (e.g. methanol, ethanol, etc.), dimethyl sulfoxide, N,N-dimethylformamide, tetrahydrofuran or any other solvent which does not adversely affect the reaction.

In case that the compound (VI) or a salt thereof or the base to be used is liquid, it can also be used as a solvent.

The reaction temperature is not critical, and the reaction can be carried out under warming or heating.

Process 6

The object compound (I-h) or a salt thereof can be prepared by reacting the compound (VII) or a salt thereof with the compound (VIII).

This reaction can be carried out in substantially the same manner as Process 4, and therefore the reaction mode and reaction conditions (e.g. solvents, bases, reaction temperature, etc.) of this reaction are to be referred to those as explained in Process 4.

Process 7

The object compound (I-j) or a salt thereof can be prepared by subjecting the compound (I-i) or a salt thereof to removal reaction of lower alkyl.

The reaction may be carried out in the presence of alkali metal halide (e.g. lithium iodide, etc.).

The reaction may be carried out in the presence of an inorganic or an organic base such as tri(lower)alkylamine (e.g. trimethylamine, triethylamine, etc.), pyridine or its derivative (e.g. picoline, lutidine, 4-dimethylaminopyridine, etc.), or the like.

This reaction is usually carried out (in a solvent such as alcohol (e.g. methanol, ethanol, etc.), dimethyl sulfoxide, N,N-dimethylformamide, tetrahydrofuran or any other solvent which does not adversely affect the reaction.

The reaction temperature is not critical, and the reaction can be carried out under warming or heating.

Among the starting compounds (II), (III), (IV) and (VII) some of them are new and such compounds can be prepared by the methods of Preparations mentioned below.

The object compound (I) of the present invention can be isolated and purified in a conventional manner, for example, extraction, precipitation, fractional crystallization, recrystallization, chromatography, and the like.

With regard to the compound (I) of the present invention, when $R^3$ is hydroxy or acyloxy and $R^4$ is hydrogen, it is preferred that the hydroxy or acyloxy at the third position of 1-benzopyran nucleus and a group of the formula:

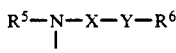

at the fourth position of the same are mutually trans, and further it is most preferred they being the (3S,4R)-isomer.

The optical resolution of the isomers of the compound (I) can be carried out by a conventional method such as a resolution by reacting a mixture of isomers with an optically active reagent. Such reagents include optically active acids (e.g., benzyloxycarbonyl-L-phenylalanine, etc.) or acid derivatives such as acid chloride (e.g., l-menthoxyacetyl chloride, etc.) or acid anydride and the like.

The object compounds (I) of the present invention are novel and exhibit pharmacological activities such as $K^+$ channel activator action (e.g. vasodilating activity, etc.) and long duration, and therefore are of use for treating or preventing vascular disorders such as hypertension, angina pectoris, cardiac insufficiency, peripheral and cerebral vascular diseases, atherosclerosis, arrhythmia, and the like.

Further, it is expected that the object compound (I) of the present invention are of use for treating or preventing disorders of smooth muscle such as ulcer, asthma, early uterine contraction and incontinence; alopecia; and the like.

In order to illustrate the usefulness of the object compound (I), pharmacological activity of representative compounds of the present invention are shown below.

[1] Test Compound (1) 4-(2-Cyanoiminothiazolin-3-yl)-6-mesyl-2,2-dimethyl-2H-1-benzopyran (2) 4-[N-[1-(Cyanoimino)ethyl]amino]-2,2-dimethyl-2H-1-benzopyran-6-carbonitrile

[2] Test Method

Male Wistar strain rats aged 10–11 weeks, weighing about 250 g were used after going unfed overnight. Under ether anesthesia, polyethylene cannula were inserted in the femoral artery for measuring blood pressure and in the femoral vein for injection of the test compound. About 2 hours after the operation, test compound was given intravenously. Blood pressure was measured at the femoral artery by means of a pressure transducer and recorded as electrically integrated values of mean arterial pressure.

[3] Test Result

Mean ratios of maximum decrease of blood pressure mmHg) are shown in Table.

| Test Compounds | Dose (mg/kg) | Effect Max (%) |
|---|---|---|
| (1) | 1.0 | 49.2 |
| (2) | 1.0 | 37.0 |

For therapeutic administration, the object compounds (I) of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases, a kind of the compound (I) to be applied, etc. In general amounts between 1 mg and about 1,000 mg or even more per day may be administered to a patient. An average single dose of about 1 mg, 2 mg, 5 mg, 10 mg, 25 mg, 50 mg, 100 mg, 200 mg of the object compound (I) of the present invention may be used in treating diseases.

The following Preparations and Examples are given for the purpose of illustrating the present invention.

PREPARATION 1

To an ice-cooled solution of 4-methoxybenzenesulfonyl chloride (25 g) in tetrahydrofuran (25 ml) was added dimethylamine (50% solution in water, 25 ml). After addition was complete, the mixture was stirred at 50° C. for 30 minutes. The reaction mixture was concentrated to give 4-methoxy-N,N-dimethylbenzenesulfonamide (38 g).

mp: 68° to 69° C.

IR (Nujol): 1380, 1160 cm$^{-1}$.

NMR (CDCl$_3$, δ): 2.68 (6H, s), 3.88 (3H, s), 6.9–7.1 (2H, m), 7.6–7.8 (2H, m).

MASS: 215, 171.

PREPARATION 2

A mixture of 4-methoxy-N,N-dimethylbenzenesulfonamide (37 g) and aluminum chloride (69 g) in benzene (170 ml) was stirred under reflux for 30 minutes. The reaction mixture was poured into ice-water and extracted with ethyl acetate. The combined organic layers were washed with water and brine, dried over anhydrous magnesium sulfate, and concentrated. The residue was purified by recrystallization from toluene to give 4-hydroxy-N,N-dimethylbenzenesulfonamide (26 g).

mp: 90° to 92° C.
IR (Nujol): 3350 cm$^{-1}$.
NMR (CDCl$_3$, δ): 2.68 (6H, s), 5.0–6.0 (1H, br m), 6.9–7.0 (2H, m), 7.5–7.7 (2H, m).
MASS: 201, 157.
Anal. Calcd. for C$_8$H$_{11}$NO$_3$S: C 47.75, H, 5.51, N 6.96 Found: C 47.83, H 5.62, N 6.75.

PREPARATION 3

A two-phase mixture of 4-hydroxy-N,N-dimethylbenzenesulfonamide (13 g), 3-chloro-3-methyl-1-butyne (33 g), tetra-n-butylammonium hydrogen sulfate (22 g), and sodium hydroxide (21 g) in a mixture of dichloromethane (195 ml) and water (97.5 ml) was vigorously stirred at room temperature for 48 hours. The organic layer was separated, washed with water and brine, dried over anhydrous magnesium sulfate, and concentrated. The residue was added to n-hexane and pulverized to give N,N-dimethyl-4-(1,1-dimethyl-2-propynyloxy)benzenesulfonamide (6.4 g).

mp: 87° to 89° C.
IR (Nujol): 3280, 3250 cm$^{-1}$. (6H, s), 7.3–7.4 (2H, m), 7.6–7.8 (2H, m).
MASS: 267, 252, 201.
Anal. Calcd. for C$_{13}$H$_{17}$NO$_3$S: C 58.40, H 6.41, N 5.24 Found: C 58.15, H 6.41, N 4.86.

PREPARATION 4

A solution of N,N-dimethyl-4-(1,1-dimethyl-2-propynyloxy)benzenesulfonamide (14 g) in 1,2-dichlorobenzene (28 ml) was stirred at 200° C. for 2 hours. After being cooled to room temperature, the reaction mixture was applied directly onto silica gel and eluted with n-hexane and then n-hexaneethyl acetate (5:1, 1:1, gradient) to give N,N,2,2-tetramethyl-2H-1-benzopyran-6-sulfonamide (12.8 g).

mp: 91° to 93° C.
IR (Nujol): 1630 cm$^{-1}$.
NMR (CDCl$_3$, δ): 1.47 (6H, s), 2.70 (6H, s), 5.71 (1H, d, J=10Hz), 6.34 (1H, d, J=10Hz), 6.85 (1H, d, J=8Hz), 7.39 (1H, d, J=2Hz), 7.50 (1H, dd, J=2Hz, 8Hz).
MASS : 267, 252, 209.
Anal. Calcd. for C$_{13}$H$_{17}$NO$_3$S: C 58.40, H 6.41, N 5.24 Found: C 58.20, H 6.34, N 4.93.

PREPARATION 5

To a vigorously stirred solution of N,N,2,2-tetramethyl-2H-1-benzopyran-6-sulfonamide (12.8 g) in the mixture of dimethyl sulfoxide (24 ml) and water (2 ml) was added N-bromosuccinimide (9.8 g) in one portion. An exothermic reaction was occurred within a few minutes and stirring was continued for an additional 10 minutes. The reaction mixture was poured into water and extracted with ethyl acetate. The combined organic layers were washed with water and brine, dried over anhydrous magnesium sulfate, and concentrated to afford trans-3-bromo-3,4-dihydro-4-hydroxy-N,N,2,2-tetramethyl-2H-1-benzopyran-6-sulfonamide (19.2 g).

mp: 154° to 155° C.
IR (Nujol): 3480 cm$^{-1}$.
NMR (CDCl$_3$, δ) : 1.44 (3H, s), 1.64 (3H, s), 2.70 (6H, s), 2.84 (1H, d, J=4Hz), 4.14 (1H, d, J=10Hz), 4.95 (1H, dd, J=4Hz, 10Hz), 6.92 (1H, d, J=8Hz), 7.62 (1H, dd, J=2Hz, 8Hz), 7.9–8.0 (1H, m).
MASS: 365, 363, 321, 319.
Anal. Calcd. for C$_{13}$H$_{18}$BrNO$_4$S: C 42.87, H 4.98, N 3.85 Found: C 42.76, H 4.85, N 3.55.

PREPARATION 6

A mixture of trans-3-bromo-3,4-dihydro-4-hydroxy-N,N,2,2-tetramethyl-2H-1-benzopyran-6-sulfonamide (19.2 g), potassium carbonate (15 g) and dimethylformamide (153 ml) was stirred at room temperature for 24 hours and followed by at 35° C. for 48 hours. The reaction mixture was poured into water and extracted with ethyl acetate. The combined organic layers were washed with water and brine, dried over anhydrous magnesium sulfate, and concentrated to give 3,4-dihydro-3,4-epoxy-N,N,2,2-tetramethyl-2H-1-benzopyran-6-sulfonamide (4.7 g).

mp: 136° to 137° C.
IR (Nujol): 1610, 1570, 1380, 1150 cm$^{-1}$.
NMR (CDCl$_3$, δ): 1.31 (3H, s), 1.61 (3H, s), 2.71. (6H, s), 3.56 (1H, d, J=4Hz), 3.97 (1H, d, J=4Hz), 6.93 (1H, d, J=8Hz), 7.66 (1H, dd, J=2Hz, 8Hz), 7.80 (1H, d, J=2Hz).
MASS: 283.
Anal. Calcd. for C$_{13}$H$_{17}$NO$_4$S: C 55.11, H 6.05, N 4.94 Found: C 55.03, H 5.97, N 5.01.

PREPARATION 7

A mixture of 3,4-dihydro-3,4-epoxy-6-mesyl-2,2-dimethyl-2H-1-benzopyran (4.0 g), ammonium hydroxide (containing ca. 28% ammonia, 40 ml), and ethanol (20 ml) was stirred at room temperature for 72 hours. The reaction mixture was concentrated, added to diisopropyl ether, and pulverized to give trans-4-amino-3,4-dihydro-3-hydroxy-6-mesyl-2,2-dimethyl-2H-1-benzopyran (4.0 g).

IR (Nujol): 3340, 3290, 3200 cm$^{-1}$.
NMR (DMSO-d$_6$, δ) : 1.10 (3H, s), 1.36 (3H, s), 3.02 (3H, s), 2.2–3.8 (3H, br m), 3.12 (1H, d, J=9Hz), 3.51 (1H, d, J=9Hz), 6.80 (1H, d, J=10Hz), 7.53 (1H, dd, J=3, 10Hz), 8.08 (1H, d, J=3Hz).

PREPARATION 8

2,2-Dimethyl-2H-1-benzopyran-6-carbonitrile (10 g) was dissolved in toluene (54 ml), and the solution was cooled to −78° C. under a nitrogen atmosphere, to this solution was added diisobutylaluminum hydride (1M solution in toluene, 81 ml) over 30 minutes, and the mixture was stirred at −78° C. for 10 minutes. The reaction mixture was quenched at −78° C. with ethyl acetate (54 ml) followed by 1M tartaric acid solution in water (100 ml). The cooling bath was removed and the mixture was vigorously stirred for 1 hour. The organic layer was separated and the aqueous layer was extracted with ethyl acetate. The combined organic layers were washed with brine, dried over anhydrous magnesium sulfate, and concentrated to give 2,2-dimethyl-2H-1-benzopyran-6-carbaldehyde (9.9 g) as a pale yellow oil, which was used without further purification.

IR (Film): 1690, 1640 cm$^{-1}$.

NMR (CDCl$_3$, δ): 1.47 (6H, s), 5.70 (1H, d, J=10Hz), 6.38 (1H, d, J=10Hz), 6.86 (1H, d, J=8Hz), 7.52 (1H, d, J=2Hz), 7.64 (1H, dd, J=2, 8Hz), 9.82 (1H, s).

MASS: 188, 173.

PREPARATION 9

To a vigorously stirred solution of 2,2-dimethyl-2H-1-benzopyran-6-carbaldehyde (8.0 g) in dimethyl sulfoxide (43 ml)-water (1.0 ml) was added N-bromosuccinimide (8.3 g) in one portion. After 10 minutes, additional N-bromosuccinimide (4.2 g) was added and the mixture was stirred for an additional 10 minutes. The reaction mixture was poured into water and extracted with ethyl acetate. The combined organic layers were washed with water and brine, dried over anhydrous magnesium sulfate, and concentrated. The residue was purified by silica gel chromatography (elution with chloroform) to give trans-3-bromo-3,4-dihydro-2,2-dimethyl-4-hydroxy-2H-1-benzopyran-6-carbaldehyde (8.0 g).

mp: 125° to 127° C.

IR (Nujol): 3380, 1680 cm$^{-1}$.

NMR (CDCl$_3$, δ): 1.45 (3H, s), 1.65 (3H, s), 2.2-3.1 (1H, br m), 4.15 (1H, d, J=10Hz), 4.98 (1H, d, J=10Hz), 6.92 (1H, d, J=8Hz), 7.77 (1H, dd, J=2, 8Hz), 8.06 (1H, br s), 9.88 (1H, s).

MASS: 286, 284, 253, 251.

Anal Calcd. for C$_{12}$H$_{13}$BrO$_3$: C 50.55, H 4.60 Found: C 50.26, H 4.66.

PREPARATION 10

A mixture of trans-3-bromo-3,4-dihydro-2,2-dimethyl-4-hydroxy-2H-1-benzopyran-6-carbaldehyde (6.9 g), potassium carbonate (6.7 g), and dimethylformamide (24 ml) was stirred at room temperature for 48 hours and followed by at 35° C. for 24 hours. The reaction mixture was poured into water and extracted with ethyl acetate. The combined organic layers were washed with water and brine, dried over anhydrous magnesium sulfate, and concentrated. The residue was purified by recrystallization from diisopropyl ether to give 3,4-dihydro-2,2-dimethyl-3,4-epoxy-2H-1-benzopyran-6-carbaldehyde (2.9 g).

mp: 108° to 110° C.

IR (Nujol): 1680 cm$^{-1}$.

NMR (CDCl$_3$, δ): 1.31 (3H, s), 1.61 (3H, s), 3.55 (1H, d. J=4Hz), 3.99 (1H, d, J=4Hz), 6.92 (1H, d, J=8Hz), 7.77 (1H, dd, J=2, 8Hz), 7.92 (1H, d, J=2Hz), 9.88 (1H, s).

MASS: 204, 189, 173.

Anal. Calcd. for C$_{12}$H$_{12}$O$_3$: C 70.57, H 5.92 Found: C 70.79, H 5.97.

PREPARATION 11

The following compound was obtained according to a similar manner to that of Preparation 5.

trans-3,6-Dibromo-3,4-dihydro-2,2-dimethyl-4-hydroxy-2H-1-benzopyran mp: 93° to 94° C.

IR (Nujol): 3200 cm$^{-1}$.

NMR (CDCl$_3$, δ): 1.39 (3H, s), 1.59 (3H, s), 2.60 (1H, br s), 4.10 (1H, d, J=9.5Hz), 4.87 (1H, d, J=9.5Hz), 6.68 (1H, d, J=8.7Hz), 7.28 (1H, dd, J=2.4, 8.7Hz), 7.59 (1H, d, J=2.4Hz).

MASS: 334, 336, 338, 200, 202.

PREPARATION 12

The following compound was obtained according to a similar manner to that of Preparation 6.

6-Bromo-3,4-dihydro-2,2-dimethyl-3,4-epoxy-2H-1-benzopyran mp: 63° to 64° C.

NMR (CDCl$_3$, δ): 1.24 (3H, s), 1.57 (3H, s), 3.48 (1H, d, J=4.3Hz), 3.84 (1H, d, J=4.3Hz), 6.69 (1H, d, J=8.6Hz), 7.32 (1H, dd, J=2.4, 8.6Hz), 7.45 (1H, d, J=2.4Hz).

MASS 254, 256.

PREPARATION 13

2,2-Dimethyl-2H-1-benzopyran-6-carbonitrile (12 g) was dissolved in tetrahydrofuran (65 ml). To this solution was added methylmagnesium bromide (3M in diethyl ether, 108 ml) dropwise at room temperature, and then the reaction mixture was stirred at reflux for 0.5 hour. After being cooled to room temperature, the mixture was poured into saturated aqueous ammonium chloride and extracted three times with ethyl acetate. The combined organic layers were washed with brine, dried over anhydrous magnesium sulfate, and concentrated. Purification of the residue by column chromatography on silica gel (elution with 10:1 n-hexane-ethyl acetate) gave 6-acetyl-2,2-dimethyl-2H-1-benzopyran (11 g).

IR (Film): 1670, 1640 cm$^{-1}$.

NMR (CDCl$_3$, δ): 1.46 (6H, s), 2.53 (3H, s), 5.66 (1H, d, J=10Hz), 6.36 (1H, d, J=10Hz), 6.79 (1H, d, J=8Hz), 7.62 (1H, d, J=2Hz), 7.74 (1H, dd, J=2, 8Hz).

MASS: 202, 187.

PREPARATION 14

The following compound was obtained according to a similar manner to that of Preparation 9.

trans-6-Acetyl-3-bromo-3,4-dihydro-2,2-dimethyl-4-hydroxy-2H-1-benzopyran mp: 112° to 113° C.

IR (Nujol): 3330, 3250, 1680 cm$^{-1}$.

NMR (CDCl$_3$, δ): 1.43 (3H, s), 1.63 (3H, s), 2.55 (3H, s), 2.8-3.8 (1H, br m), 4.13 (1H, d, J=9Hz), 4.94 (1H, d, J=9Hz), 6.84 (1H, d, J=9Hz), 7.83 (1H, dd, J=2, 9Hz), 8.14 (1H, m).

MASS: 300, 298, 285, 283, 267, 265.

Anal Calcd. for C$_{13}$H$_{15}$BrO$_3$: C 52.19, H 5.05 Found: C 51.75, H 4.90.

PREPARATION 15

The following compound was obtained according to a similar manner to that of Preparation 10.

6-Acetyl-3,4-dihydro-2,2-dimethyl-3,4-epoxy-2H-1-benzopyran mp: 71° to 72° C.

IR (Nujol): 1680 cm$^{-1}$.

NMR (CDCl$_3$, δ): 1.29 (3H, s), 1.60 (3H, s), 2.57 (3H, s), 3.54 (1H, d, J=4Hz), 3.97 (1H, d, J=4Hz), 6.85 (1H, d, J=8Hz), 7.87 (1H, dd, J=2,8Hz), 8.01 (1H, d, J=2Hz).

MASS: 218, 203.

Anal. Calcd for C$_{13}$H$_{14}$O$_3$: C 71.54, H 6.47 Found: C 71.21, H 6.48.

PREPARATION 16

The following compound was obtained according to a similar manner to that of Preparation 3.

3-Methyl-3-(4-methylphenoxy)-1-butyne

IR (Film): 3250, 2100 cm$^{-1}$.
NMR (CDCl$_3$, δ): 1.72 (6H, s), 2.68 (1H, s), 3.05 (3H, s), 7.3-7.4 (2H, m), 7.8-7.9 (2H, m).
MASS: 238, 223.

PREPARATION 17

To 1,2-dichlorobenzene (230 ml) at 200° C. was added 3-methyl-3-(4-mesylphenoxy)-1-butyne (130 g) dropwise over a period of 1.5 hours. The reaction mixture was stirred at 200° C. for an additional 2 hours followed by removal of 1,2-dichlorobenzene by distillation under reduced pressure. The residue was dissolved in diisopropyl ether (100 ml) and treated with activated carbon. The mixture was filtered and the filtrate afforded the precipitate, which was collected, washed with diisopropyl ether, and dried to give 2,2-dimethyl-6-mesyl-2H-1-benzopyran (77 g).

mp: 69° to 71° C.
IR (Nujol): 1640 cm$^{-1}$.
NMR (CDCl$_3$, δ): 1.47 (6H, s), 3.03 (3H, s), 5.73 (1H, d, J=10Hz), 6.34 (1H, d, J=10Hz), 6.87 (1H, d, J=8Hz) 7.54 (1H, d, J=2Hz) 7.65 (1H, dd, J=2, 8Hz).
Anal. Calcd. for C$_{12}$H$_{14}$O$_3$S: C 60.48, H 5.92 Found: C 60.41, H 6.06.

PREPARATION 18

2,2-Dimethyl-2H-1-benzopyran-6-carbonitrile (12 g) was dissolved in tetrahydrofuran (65 ml). To this solution was added methylmagnesium bromide (3M in diether ether, 108 ml) dropwise at room temperature, and then the reaction mixture was stirred at reflux for 0.5 hour. After being cooled to room temperature, the mixture was poured into saturated aqueous ammonium chloride and extracted three times with ethyl acetate. The combined organic layers were washed with brine, dried over anhydrous magnesium sulfate, and concentrated. Purification of the residue by column chromatography on silica gel (elution with 10:1 n-hexane-ethyl acetate) gave 6-acetyl-2,2-dimethyl-2H-1-benzopyran (11 g).

IR (Film): 1670, 1640 cm$^{-1}$.
NMR (CDCl$_3$, δ): 1.46 (6H, s), 2.53 (3H, s), 5.66 (1H, d, J=10Hz), 6.36 (1H, d, J=10Hz), 6.79 (1H, d, J=8Hz), 7.62 (1H, d, J=2Hz), 7.74 (1H, dd, J=2, 8Hz).
MASS: 202, 187.

PREPARATION 19

The following compounds were obtained according to a similar manner to that of Preparation 5.
(1) trans-3-Bromo-3,4-dihydro-4-hydroxy-2,2-dimethyl-6-mesyl-2H-1-benzopyran
  mp: 141°-143° C.
  IR (Nujol): 3450 cm$^{-1}$.
  NMR (CDCl$_3$, δ): 1.38 (3H, s), 1.58 (3H, s), 3.00 (3H, s), 3.24 (1H, d, J=5Hz), 4.06 (2H, d, J=9Hz), 4.89 (1H, dd, J=5, 9Hz), 6.85 (1H, d, J=9Hz), 7.67 (1H, dd, J=3, 9Hz), 8.05 (1H, d, J=3Hz).
(2) trans-6-Acetyl-3-bromo-3,4-dihydro-4-hydroxy-2,2-dimethyl-2H-1-benzopyran
  mp: 112° to 113° C.
  IR (Nujol): 3330, 3250, 1680 cm$^{-1}$.
  NMR (CDCl$_3$, δ): 1.43 (3H, s), 1.63 (3H, s), 2.55 (3H, s), 2.8-3.8 (1H, br m), 4.13 (1H, d, J=9Hz), 4.94 (1H, d, J=9Hz), 6.84 (1H, d, J=9Hz), 7.83 (1H, dd, J=2, 9Hz), 8.14 (1H, m).
  MASS: 300, 298, 285, 283, 267, 265.
  Anal. Calcd. for C$_{13}$H$_{15}$BrO$_3$: C 52.19, H 5.05 Found: C 51.75, H 4.90.

PREPARATION 20

The following compounds were obtained according to a similar manner to that of Preparation 6.
(1) 3,4-Dihydro-2,2-dimethyl-3,4-epoxy-6-mesyl-2H-1-benzopyran
  mp: 153°-155° C.
  NMR (CDCl$_3$, δ): 1.23 (3H, s), 1.53 (3H, s), 2.95 (3H, s), 3.46 (1H, d, J=5Hz), 3.86 (1H, d, J=5Hz), 6.83 (1H, d, J=9Hz), 7.68 (1H, dd, J=3, 9Hz), 7.83 (1H, d, J=3Hz).
(2) 6-Acetyl-3,4-dihydro-2,2-dimethyl-3,4-epoxy-2H-1-benzopyran
  mp: 71°-72°° C.
  IR (Nujol): 1680 cm$^{-1}$.
  NMR (CDCl$_3$, δ): 1.29 (3H, s), 1.60 (3H, s), 2.57 (3H, s), 3.54 (1H, d, J=4Hz), 3.97 (1H, d, J=4Hz), 6.85 (1H, d, J=8Hz), 7.87 (1H, dd, J=2, 8Hz), 8.01 (1H, d, J=2Hz).
  MASS: 218, 203.
  Anal. Calcd. for C$_{13}$H$_{14}$O$_3$: C 71.54, H 6.47 Found: C 71.21, H 6.48.

PREPARATION 21

The following compounds were obtained according to a similar manner to that of Preparation 7.
(1) trans-4-Amino-3,4-dihydro-3-hydroxy-N,N,2,2-tetramethyl-2H-1-benzopyran-6-sulfonamide
  mp: 183° to 184° C.
  IR (Nujol): 3360, 3280 cm$^{-1}$.
  NMR (DMSO-d$_6$, δ): 1.13 (3H, s), 1.40 (3H, s), 2.00 (2H, s), 2.57 (6H, s), 3.22 (1H, dd, J=5, 9Hz), 3.56 (1H, d, J=9Hz), 5.56 (1H, d, J=5Hz), 6.90 (1H, d, J=8Hz), 7.45 (1H, dd, J=2, 8Hz), 7.97 (1H, d, J=2Hz).
  MASS: 300, 282, 267.
  Anal. Calcd. for C$_{13}$H$_{20}$N$_2$O$_4$S: C 51.98, H 6.71, N 9.33 Found: C 51.77, H 6.57, N 9.09.
(2) trans-4-Amino-3,4-dihydro-3-hydroxy-2,2-dimethyl-6-nitro-2H-1-benzopyran
  mp: 150° to 151° C.
  IR (Nujol): 3350, 3280, 3070, 1500 cm$^{-1}$.
  NMR (DMSO-d$_6$, δ): 1.15 (3H, s), 1.42 (3H, s), 1.99 (2H, br s), 3.24 (1H, dd, J=5, 9Hz), 3.59 (1H, d, J=9Hz), 5.63 (1H, d, J=5Hz), 6.90 (1H, d, J=9Hz), 8.00 (1H, dd, J=3, 9Hz), 8.50 (1H, dd, J=1, 3Hz).
  MASS: 222 (M$^+$-16), 208.
  Anal. Calcd. for C$_{11}$H$_{14}$N$_2$O$_4$: C 55.46, H 5.92, N 11.76 Found: C 55.13, H 5.93, N 11.66.
(3) trans-6-Acetyl-4-amino-3,4-dihydro-3-hydroxy-2,2-dimethyl-2H-1-benzopyran
  mp: 134° to 135° C.
  IR (Nujol): 3350, 3290, 3100, 1650 cm$^{-1}$.
  NMR (CDCl$_3$, δ): 1.24 (3H, s), 1.54 (3H, s), 1.6-2.5 (3H, br m), 2.56 (3H, s), 3.36 (1H, d, J=10Hz), 3.68 (1H, br d, J=10Hz), 6.82 (1H, d, J=8Hz), 7.77 (1H, dd, J=2, 8Hz), 8.06 (1H, dd, J=1, 2Hz).
  MASS: 235, 220.
  Anal. Calcd. for C$_{13}$H$_{17}$NO$_3$: C 66.36, H 7.28, N 5.95 Found: C 65.86, H 7.15, N 5.92.
(4) trans-4-Amino-6-bromo-3,4-dihydro-3-hydroxy-2,2-dimethyl-2H-1-benzopyran
  mp: 130° to 131° C.
  IR (Nujol): 3370, 3280, 3100 cm$^{-1}$.
  NMR (DMSO-d$_6$, δ): 1.08 (3H, s), 1.36 (3H, s), 3.26 (1H, d, J=9.4Hz), 3.65 (1H, d, J=9.4Hz), 4.26 (2H, br s), 5.58 (1H, br s), 6.69 (1H, d, J=8Hz), 7.27 (1H, dd, J=2.5, 8.7Hz), 7.71 (1H, br s).
  MASS: 271, 273.

(5) trans-3,4-Dihydro-2,2-dimethyl-3-hydroxy-4-methylamino-2H-1-benzopyran-6-carbonitrile mp: 117° to 119° C.

NMR (DMSO-d$_6$, δ): 1.13 (3H, s), 1.42 (3H, s), 2.14 (3H, s), 2.44 (1H, br s), 3.62 (2H, m), 5.43 (1H, br s), 6.88 (1H, d, J=8.5Hz), 7.55 (1H, dd, J=8.5, 2.1Hz), 7.85 (1H, d, J=2.1Hz).

(6) trans-4-Amino-3,4-dihydro-3-hydroxy-2,2,6-trimethyl-2H-1-benzopyran

NMR (DMSO-d$_6$, δ): 1.05 (3H, s), 1.34 (3H, s), 2.21 (3H, s), 2.1 (2H, br s), 3.16 (1H, d, J=9.3Hz), 3.48 (1H, d, J=9.3Hz), 5.3 (1H, br), 6.57 (1H, d, J=8.2Hz), 6.88 (1H, dd, J=8.2, 1.8Hz), 7.35 (1H, br s).

MASS: 207, 135.

(7) Ethyl trans-4-amino-3,4-dihydro-3-hydroxy-2,2-dimethyl-2H-1-benzopyran-6-carboxylate mp: 233° C. (dec.).

IR (Nujol): 3360, 3275, 3140, 1710, 1610 cm$^{-1}$.

NMR (DMSO-d$_6$, δ): 1.12 (3H, s), 1.31 (3H, t, J=7.1Hz), 1.40 (3H, s), 2.40 (2H, br s), 3.21 (1H, d, J=9.4Hz), 3.56 (1H, d, J=9.4Hz), 4.28 (2H, quartet, J=7.1Hz), 5.5 (1H, br s), 6.79 (1H, d, J=8.5Hz), 7.71 (1H, dd, J=8.5, 2.1Hz), 8.25 (1H, br s).

MASS: 265, 194, 148.

EXAMPLE 1

A mixture of 3,4-dihydro-3,4-epoxy-6-mesyl-2,2-dimethyl-2H-1-benzopyran (1.5 g), 2-(cyanoimino)-thiazolidine (1.1 g), triethylamine (3 ml) and N,N-dimethylformamide (6 ml) was stirred at 100° C. for 5 hours. After cooling, the reaction mixture was poured into water. The precipitate was collected by filtration, washed well with water and dried in vacuo to give trans-4-(2-cyanoiminothiazolidin-3-yl)-3,4-dihydro-3-hydroxy-6-mesyl-2,2-dimethyl-2H-1-benzopyran (1.6 g).

mp: 304° to 307° C.

IR (Nujol): 3350, 2190 cm$^{-1}$.

NMR (DMSO-d$_6$, δ): 1.19 (3H, s), 1.45 (3H, s), 3.17 (3H, s), 3.3-4.1 (5H, m), 5.25 (1H, d, J=9Hz), 5.99 (1H, d, J=6Hz), 7.10 (1H, d, J=9Hz), 7.45 (1H, m), 7.77 (1H, m).

MASS: 381, 363, 348.

Anal. Calcd. for C$_{16}$H$_{19}$N$_3$O$_4$S$_2$: C 50.38, H 5.02, N 11.02, S 16.81 Found: C 50.42, H 4.96, N 11.05, S 16.81.

EXAMPLE 2

A mixture of trans-4-(2-cyanoiminothiazolidin-3-yl)-3,4-dihydro-3-hydroxy-6-mesyl-2,2-dimethyl-2H-1-benzopyran (5.5 g) and acetic anhydride (25 ml) in pyridine (50 ml) was allowed to stand at room temperature overnight. The mixture was concentrated to give a residue of trans-3-acetoxy-4-[2-(cyanoimino)thiazolidin-3-yl]-3,4-dihydro-6-mesyl-2,2-dimethyl-2H-1-benzopyran, which was washed with diisopropyl ether and dried in vacuo. To a suspension of this residue in toluene (21 ml) was added 1,8-diazabicyclo[5.4.0]undec-7-ene (10.5 ml), and the mixture was stirred at 100° C. for 1 hour. After cooling, the reaction mixture was poured into water, extracted with ethyl acetate, washed with water, dried over anhydrous magnesium sulfate and concentrated. The residue was purified by silica gel chromatography using ethyl acetate as an eluent to afford 4-(2-cyanoiminothiazolidin-3-yl)-6-mesyl-2,2-dimethyl-2H-1-benzopyran as a white solid. Recrystallization from 50% aqueous acetonitrile gave the pure product (1.44 g).

mp: 247° to 249° C.

IR (Nujol): 2170, 1640 cm$^{-1}$.

NMR (DMSO-d$_6$, δ): 1.47 (6H, s), 3.19 (3H, s), 3.6-3.8 (2H, m), 4.1-4.3 (2H, m), 6.22 (1H, s), 7.06 (1H, d, J=9Hz), 7.45 (1H, d, J=2Hz), 7.74 (1H, dd, J=2Hz, 9Hz).

MASS: 363, 348.

Anal. Calcd. for C$_{16}$H$_{17}$N$_3$O$_3$S$_2$: C 52.87, H 4.71, N 11.56, S 17.64 Found: C 52.92, H 5.18, N 11.77, S 17.85.

EXAMPLE 3

To a solution of 3,4-dihydro-3,4-epoxy-6-mesyl-2,2-dimethyl-2H-1-benzopyran (1.5 g) in dimethyl sulfoxide (30 ml) was added sodium salt of isothiazolidine 1,1-dioxide (1.7 g). The mixture was stirred at room temperature overnight. Water was carefully added to the reaction mixture and the whole was extracted with ethyl acetate. The extract was washed with water, dried over anhydrous magnesium sulfate, and evaporated in vacuo. The residue was purified by column chromatography on silica gel (50 g) with a mixture of chloroform and methanol (50:1) as eluents to give trans-3,4-dihydro-3-hydroxy-4-(1,1-dioxoisothiazolidin-2-yl)-6-mesyl-2,2-dimethyl-2H-1-benzopyran (0.47 g).

mp: 220° to 221° C.

IR (Nujol): 3420 cm$^{-1}$.

NMR (DMSO-d$_6$, δ): 1.17 (3H, s), 1.45 (3H, s), 2.0-2.5 (2H, m), 2.6-3.0 (2H, s), 3.0-3.4 (2H, m), 3.12 (3H, s), 3.68 (1H, d, J=9Hz), 4.48 (1H, d, J=9Hz), 5.64 (1H, s), 6.92 (1H, d, J=9Hz), 7.6-7.8 (1H, m), 7.8-7.9 (1H, m).

EXAMPLE 4

A solution of trans-3,4-dihydro-3-hydroxy-4-(1,1-dioxoisothiazolidin-2-yl)-6-mesyl-2,2-dimethyl-2H-1-benzopyran (0.32 g) in pyridine (10 ml) was treated with acetic anhydride (5 ml), and the mixture was stood at room temperature overnight. The reaction mixture was poured into water and extracted with ethyl acetate. The extract was washed successively with 1N hydrochloric acid, a saturated aqueous solution of sodium bicarbonate and brine, and then dried over anhydrous magnesium sulfate. Removal of the solvent under reduced pressure gave the crude product, which was purified by recrystallization from ethyl acetate to give 4-(1,1-dioxoisothiazolidin-2-yl)-6-mesyl-2,2-dimethyl-2H-1-benzopyran (0.14 g).

mp: 226° to 227° C.

IR (Nujol): 1640 cm$^{-1}$.

NMR (CDCl$_3$, δ): 1.50 (6H, s), 2.3-2.6 (2H, m), 3.2-3.6 (4H, m), 5.93 (1H, s), 6.88 (1H, d, J=9Hz), 7.70 (1H, dd, J=3, 9Hz), 7.83 (1H, d, J=3Hz).

EXAMPLE 5

The following compound was obtained according to a similar manner to that of Example 1.

trans-4-(2-Cyanoiminothiazolidin-3-yl)-3,4-dihydro-3-hydroxy-N,N,2,2-tetramethyl-2H-1-benzopyran-6-sulfonamide mp: >300° C.

IR (Nujol): 3300, 2180 cm$^{-1}$.

NMR (DMSO-d$_6$, δ): 1.20 (3H, s), 1.47 (3H, s), 2.56 (6H, s), 3.3-3.5 (3H, m), 3.8-4.0 (2H, m), 5.2-5.4 (1H, m), 6.0-6.1 (1H, m), 7.08 (1H, d, J=8Hz), 7.16 (1H, br s), 7.5-7.7 (1H, m).

MASS: 410, 367.

Anal. Calcd. for C$_{17}$H$_{22}$N$_4$O$_4$S$_2$: C 49.74, H 5.40, N 13.65, S 15.62 Found: C 49.68, H 5.34, N 13.40, S 15.81.

EXAMPLE 6

The following compound was obtained according to a similar manner to that of Example 2.

4-(2-Cyanoiminothiazolidin-3-yl)-N,N2,2-tetramethyl-2H-1-benzopyran-6-sulfonamide mp: 244° to 245° C.

IR (Nujol): 2180, 1660 cm$^{-1}$.

NMR (DMSO-d$_6$, δ): 1.47 (6H, s), 2.57 (6H, s), 3.6–3.8 (2H, m), 4.2–4.4 (2H, m), 6.22 (1H, s), 7.06 (1H, d, J=8Hz), 7.20 (1H, d, J=2Hz), 7.57 (1H, dd, J=2Hz, 8Hz).

MASS: 392, 377, 349.

Anal. Calcd. for $C_{17}H_{20}N_4O_3S_2$: C 52.02, H 5.14, N 14.27, S 16.34 Found: C 51.97, H 5.01, N 14.11, S 16.30.

EXAMPLE 7

A solution of trans-4-amino-3,4-dihydro-3-hydroxy-6-mesyl-2,2-dimethyl-2H-1-benzopyran (3.7 g), dimethyl N-cyanoiminodithiocarbonate [(CH$_3$S)$_2$C=NCN] (2.1 g), and pyridine (14 ml) was stirred under reflux for 3 hours. After being cooled to room temperature, the reaction mixture was concentrated, added to ethyl acetate, and pulverized to give trans-4-(3-cyano-2-methyl-1-isothioureido)-3,4-dihydro-3-hydroxy-6-mesyl-2,2-dimethyl-2H-1-benzopyran (2.7 g).

mp: 219° to 220° C.

IR (Nujol): 3580, 3460, 3380, 3320, 2170 cm$^{-1}$.

NMR (DMSO-d$_6$, δ): 1.09 (3H, s), 1.35 (3H, s), 2.54 (3H, s), 3.07 (3H, s), 3.72 (1H, dd, J=6, 9Hz), 4.05 (1H, t-like, J=ca. 9Hz), 5.84 (1H, d, J=6Hz), 6.95 (1H, d, J=9Hz), 7.50 (1H, br s), 7.65 (1H, dd, J=3, 9Hz), 8.55 (1H, d, J=6Hz).

Anal. Calcd. for $C_{15}H_{19}N_3O_4S_2$: C 46.50, H 5.46, N 10.84, S 16.55 Found: C 46.14, H 5.41, N 10.86, S 16.48.

EXAMPLE 8

A mixture of trans-4-(3-cyano-2-methyl-1-isothioureido)-3,4-dihydro-3-hydroxy-6-mesyl-2,2-dimethyl-2H-1-benzopyran (1.0 g) and 40% aqueous methylamine 10 ml) was stirred at 40° C. for 8 hours. The resulting precipitate was collected, washed with ethanol, and dried.

Recrystallization from ethanol gave trans-4-(2-cyano-3-methyl-1-guanidino)-3,4-dihydro-3-hydroxy-6-mesyl-2,2-dimethyl-2H-1-benzopyran (0.35 g).

mp: 166° to 168° C.

IR (Nujol): 3330, 2170 cm$^{-1}$.

NMR (DMSO-d$_6$, δ): 1.00 (3H, s), 1.23 (3H, s), 2.59 (3H, d, J=4Hz), 2.95 (3H, s), 3.54 (1H, dd, J=6, 10Hz), 4.69 (1H, t, J=6Hz), 5.56 (1H, d, J=6Hz), 6.80 (1H, d, J=9Hz), 6.9–7.3 (2H, m), 7.04 (1H, d, J=6Hz), 7.47 (1H, s), 7.58 (1H, d, J=2Hz).

EXAMPLE 9

The following compound was obtained according to a similar manner to that of Example 8.

trans-4-(2-Cyano-3,3dimethyl-1-guanidino)-3,4-dihydro-3-hydroxy-6-mesyl-2,2-dimethyl-2H-1-benzopyran mp: 265° to 268° C.

IR (Nujol): 3360, 3200, 2180 cm$^{-1}$.

NMR (DMSO-d$_6$, δ): 1.16 (3H, s), 1.40 (3H, s), 3.00 (6H, s), 3.09 (3H, s), 3.66 (1H, dd, J=6, 9Hz), 5.02 (1H, t-like, J=ca. 9Hz), 5.76 (1H, d, J=6Hz), 6.95 (1H, d, J=9Hz), 7.21 (1H, d, J=9Hz), 7.67 (1H, dd, J=3, 9Hz), 7.7–7.9 (1H, m).

Anal. Calcd. for $C_{16}H_{22}N_4O_4S$: C 52.44, H 6.05, N 15.29 Found: C 52.52, H 5.88, N 15.32.

EXAMPLE 10

The following compounds were obtained according to a similar manner to that of Example 1.

(1) trans-4-(2-Cyanoiminothiazolidin-3-yl)-3,4-dihydro-2,2-dimethyl-3-hydroxy-2H-1-benzopyran-6-carbaldehyde mp: 270° to 271° C.

IR (Nujol): 3290, 2170, 1680 cm$^{-1}$.

NMR (DMSO$_6$, δ): 1.20 (3H, s), 1.47 (3H, s), 3.4–3.6 (3H, m), 3.8–4.0 (2H, m), 5.29 (1H, d, J=10Hz), 6.04 (1H, d, J=7Hz), 7.01 (1H, d, J=8Hz), 7.53 (1H, br s), 7.7–7.8 (1H, m), 9.88 (1H, s).

MASS: 331, 313, 298.

Anal. Calcd. for $C_{16}H_{17}N_3O_3S$: C 58.00, H 5.17, N 12.68, S 9.68 Found: C 57.59, H 5.11, N 12.80, S 9.60.

(2) trans-6-Bromo-4-(2-cyanoiminothiazolidin-3-yl)-3,4-dihydro-2,2-dimethyl-3-hydroxy-2H-1-benzopyran mp: 237° to 239° C. (dec.).

IR (Nujol): 3260, 2195, 1580, 1080 cm$^{-1}$.

NMR (DMSO-d$_6$, δ): 1.15 (3H, s), 1.42 (3H, s), 3.4–3.65 (3H, m), 3.7–3.95 (2H, m), 5.21 (1H, d, J=10.0Hz), 5.94 (1H, d, J=5.7Hz), 6.80 (1H, d, J=8.6Hz), 7.04 (1H, br s), 7.37 (1H, d, J=8.6Hz).

MASS: 382, 384, 363, 365, 348, 350.

Anal. Calcd. for $C_{15}H_{16}BrN_3O_2S$: C 47.13, H 4.22, N 10.96 Found: C 47.23, H 4.36, N 10.96.

(3) trans-6-Acetyl-4-(2-cyanoiminothiazolidin-3-yl)-3,4-dihydro-2,2-dimethyl-3-hydroxy-2H-1-benzopyran mp 197° to 198° C.

IR (Nujol): 3390, 2180, 1670 cm$^{-1}$.

NMR (DMSO-$_6$, δ): 1.19 (3H, s), 1.47 (3H, s), 2.51 (3H, s), 3.4–3.7 (3H, m), 3.7–4.0 (2H, m), 5.27 (1H, d, J=10Hz), 6.00 (1H, d, J=5Hz), 6.94 (1H, d, J=9Hz), 7.45 (1H, br s), 7.85 (1H, br d, J=10Hz).

MASS: 327 (M$^+$-18), 312.

Anal. Calcd. for $C_{17}H_{19}N_3O_3S$: C 59.11, H 5.54, N 12.16, S 9.28 Found: C 59.52, H 5.56, N 12.21, S 9.25.

(4) trans-4-(2-Cyanoiminothiazolidin-3-yl)-3,4-dihydro-2,2-dimethyl-3-hydroxy-6-nitro-2H-1-benzopyran mp: 264° to 266° C.

IR (Nujol): 3250, 3100, 2180 cm$^{-1}$.

NMR (DMSO-d$_6$, δ): 1.22 (3H, s), 1.49 (3H, s), 3.55 (4H, br s), 3.90 (1H, br s), 5.30 (1H, br d, J=10Hz), 6.10 (1H, br d, J=6Hz), 7.05 (1H, d, J=8Hz), 7.73 (1H, br s), 8.10 (1H, dd, J=2, 8Hz).

MASS: 348, 330, 315.

Anal. Calcd. for $C_{15}H_{16}N_4O_4S$: C 51.72, H 4.63, N 16.08 Found: C 51.36, H 4.71, N 15.12.

(5) Ethyl trans-4-(2-cyanoiminothiazolidin-3-yl)-3,4-dihydro-2,2-dimethyl-3-hydroxy-2H-1-benzopyran-6-carboxylate mp: 245° to 247° C.

IR (Nujol): 3390, 2180, 1695, 1610 cm$^{-1}$.

NMR (DMSO-d$_6$, δ): 1.18 (3H, s), 1.29 (3H, t, J=7.0Hz), 1.46 (3H, s), 3.3–3.7 (3H, m), 3.7–4.1 (2H, m), 4.28 (2H, q, J=7.0Hz), 5.28 (1H, d, J=10.0Hz), 6.01 (1H, d, J=5.7Hz), 6.94 (1H, d, J=8.6Hz), 7.46 (1H, br s), 7.79 (1H, br d, J=8.6Hz).

MASS: 375, 357, 342, 296.

Anal. Calcd. for $C_{18}H_{21}N_3O_4S$: C 57.59, H 5.64, N 11.19 Found: C 57.41, H 5.52, N 11.17.

EXAMPLE 11

The following compounds were obtained according to a similar manner to that of Example 2.

(1) 4-(2-Cyanoiminothiazolidin-3-yl)-2,2-dimethyl-2H-1-benzopyran-6-carbaldehyde mp: 230° to 231° C.

IR (Nujol): 2180, 1680, 1650 cm$^{-1}$.

NMR (DMSO-d$_6$, δ): 1.48 (6H, s), 3.72 (2H, br t, J=7Hz), 4.20 (2H, t, J=7Hz), 6.19 (1H, s), 7.03 (1H, d, J=8Hz), 7.55 (1H, d, J=2Hz), 7.78 (1H, dd, J=2, 8Hz), 9.88 (1H, s).

MASS: 313, 298, 270.

Anal. Calcd. for C$_{17}$H$_{15}$N$_3$O$_2$S: C 61.32, H 4.82, N 13.41, S 10.23 Found: C 61.14, H 4.79, N 13.05, S 10.36.

(2) 6-Bromo-4-(2-cyanoiminothiazolidin-3-yl)-2,2-dimethyl-2H-1-benzopyran mp: 205° to 207° C.

IR (Nujol): 2180, 1660 cm$^{-1}$.

NMR (DMSO-d$_6$, δ): 1.42 (6H, s), 3.70 (2H, br t, J=7.4Hz), 4.17 (2H, t, J=7.4Hz), 6.12 (1H, s), 6.81 (1H, d, J=8.6Hz), 7.17 (1H, d, J=2.4Hz), 7.36 (1H, dd, J=2.4, 8.6Hz).

MASS: 363, 365, 348, 350.

Anal. Calcd. for C$_{15}$H$_{14}$BrN$_3$OS: C 49.46, H 3.87, N 11.54 Found: C 49.37, H 3.86, N 11.23.

(3) 6-Acetyl-4-(2-cyanoiminothiazolidin-3-yl)-2,2-dimethyl-2H-1-benzopyran mp: 209° to 211° C.

IR (Nujol): 2180, 1680 cm$^{-1}$.

NMR (DMSO-d$_6$, δ): 1.46 (6H, s), 2.52 (3H, s), 3.72 (2H, t, J=7Hz), 4.20 (2H, t, J=7Hz), 6.16 (1H, s), 6.96 (1H, d, J=8Hz), 7.48 (1H, d, J=2Hz), 7.86 (1H, dd, J=2, 8Hz).

MASS: 327, 312.

Anal. Calcd. for C$_{17}$H$_{17}$N$_3$O$_2$S: C 62.37, H 5.23, N 12.83 Found: C 62.69, H 5.31, N 12.75.

(4) 4-(2-Cyanoiminothiazolidin-3-yl)-2,2-dimethyl-6-nitro-2H-1-benzopyran mp: 212° to 213° C.

IR (Nujol): 2190, 1660 cm$^{-1}$.

NMR (DMSO-d$_6$, δ): 1.49 (6H, s), 3.74 (2H, br t, J=7Hz), 4.24 (2H, t, J=7Hz), 6.30 (1H, s), 7.06 (1H, d, J=8Hz), 7.79 (1H, d, J=2Hz), 8.11 (1H, dd, J=2, 8Hz).

MASS: 330, 315.

Anal. Calcd. for C$_{15}$H$_{14}$N$_4$O$_3$S: C 54.54, H 4.27, N 16.96, S 9.71 Found: C 54.49, H 4.39, N 15.98, S 9.86.

EXAMPLE 12

A mixture of trans-4-amino-3,4-dihydro-2,2-dimethyl-3-hydroxy-2H-1-benzopyran-6-carbonitrile (15.28 g) and ethyl N-cyanoacetimidate (9.42 g) in pyridine (70 ml) was refluxed under nitrogen atmosphere for 9 hours. The mixture was cooled to room temperature and concentrated under reduced pressure. The residue was dissolved in ethyl acetate (150 ml), washed with 5% hydrochloric acid (100 ml), water (100 ml), and brine (100 ml), successively. The organic layer was dried over anhydrous magnesium sulfate and concentrated under reduced pressure. The residue was recrystallized from ethyl acetate to give trans-4-[N-[1-(cyanoimino)ethyl]amino]-3,4-dihydro-2,2-dimethyl-3-hydroxy-2H-1-benzopyran-6-carbonitrile (12.68 g).

mp: 236°-238° C.

NMR (DMSO-d$_6$, δ): 1.19 (3H, s), 1.42 (3H, s), 2.35 (3H, s), 3.59 (1H, dd, J=9, 5.5Hz), 4.99 (1H, t, J=9Hz), 5.85 (1H, d, J=5.5Hz), 6.94 (1H, d, J=9Hz), 7.55-7.7 (2H, m), 9.14 (1H, d, J=9Hz).

MASS: 266, 251, 210.

EXAMPLE 13

A mixture of trans-4-[N-[1-(cyanoimino)ethyl]amino]-3,4-dihydro-2,2-dimethyl-3-hydroxy-2H-1-benzopyran-6-carbonitrile (0.53 g) and acetic anhydride (0.38 g) in dry pyridine (2.65 ml) was stirred at room temperature for 8 hours. The reaction mixture was concentrated under reduced pressure and the residue was dissolved in ethyl acetate, washed with 5% hydrochloric acid, saturated aqueous sodium bicarbonate, and brine, successively. The extract was dried over anhydrous magnesium sulfate and concentrated under reduced pressure. The residue was pulverized with diisopropyl ether and collected by filtration to give trans-3-acetoxy-4-[N-[1-(cyanoimino)-ethyl]amino]-3,4-dihydro-2,2-dimethyl-2H-1-benzopyran-6-carbonitrile (0.55 g).

mp: 236°-237.5° C.

IR (Nujol): 3225, 3100, 2225, 2160, 1745 cm$^{-1}$.

NMR (DMSO-d 6): 1.27 (3H, s), 1.35 (3H, s), 2.09 (3H, s), 2.28 (3H, s), 5.05-5.25 (2H, m), 7.02 (1H, d, J=8.5Hz), 7.70 (1H, dd, J=8.5, 2Hz), 7.77 (1H, br s), 9.22 (1H, s).

Mass: 266, 251, 210.

EXAMPLE 14

A mixture of trans-3-acetoxy-4-[N-[1-(cyanoimino)-ethyl]amino]-3,4-dihydro-2,2-dimethyl-2H-1-benzopyran-6-carbonitrile (0.49 g) and 1,8-diazabicyclo[5.4.0]-7-undecene (0.46 g) in toluene 10 ml) was stirred at 80° C. for 4 hours, at 90° C. for 2 hours and at 100° C. for additional 2 hours. The resulting mixture was concentrated under reduced pressure. The residue was dissolved in ethyl acetate and then washed with 5% hydrochloric acid, aqueous saturated sodium bicarbonate solution, and brine, successively. The organic layer was dried over anhydrous magnesium sulfate and concentrated under reduced pressure. The residue (0.31 g) was subjected to column chromatography on silica gel (31 g) and eluted with a mixture of chloroform and methanol (40:1). The fractions containing the desired compound were collected and concentrated under reduced pressure to give powders (0.21 g), which were recrystallized from ethanol to give 4-[N-[1-(cyanoimino)ethyl]amino]-2,2-dimethyl-2H-1-benzopyran-6-carbonitrile (0.17 g).

mp: 205°-206° C.

IR (Nujol): 3200, 3050, 2230, 2190, 1640, 1580 cm$^{-1}$.

NMR (DMSO-d$_6$, δ): 1.45 (6H, s), 2.42 (3H, s), 6.06 (1H, s), 6.97 (1H, d, J=8.3Hz), 7.65 (1H, dd, J=8.3Hz, J=2Hz), 7.69 (1H, d, J=2Hz), 10.02 (1H, s).

MASS: 266, 251, 224, 210.

Anal. Calcd. for C$_{15}$H$_{14}$N$_4$O: C 67.65, H 5.30, N 21.04 Found: C 67.89, H 5.30, N 21.05.

EXAMPLE 15

A mixture of trans-4-amino-3,4-dihydro-2,2-dimethyl-3-hydroxy-2H-1-benzopyran-6-carbonitrile (4.37 g) and ethyl N-cyanopropionimidate (2.65 g) in ethanol (22 ml) was refluxed for 10 hours. The mixture was cooled and concentrated under reduced pressure. The residue was pulverized with ethanol and recrystallized from ethanol to give trans-4-[N-[1-(cyanoimino)propyl]amino]-3,4-dihydro-2,2-dimethyl-3-hydroxy-2H-1-benzopyran-6-carbonitrile (2.81 g).

mp: 122° to 124° C.

IR (Nujol): 3370, 3300, 2230, 2180 cm$^{-1}$.

NMR (DMSO-d$_6$, δ): 1.18 (3H, s), 1.27 (3H, t, J=7.6Hz), 2.60 (2H, quartet, J=7.6Hz), 3.63 (1H, dd, J=9.3Hz), 4.95 (1H, br t, J=8.4Hz), 5.85 (1H, d, J=5.9Hz), 6.96 (1H, d, J=8.5Hz), 7.53 (1H, br s), 7.64 (1H, dd, J=8.5Hz), 9.05 (1H, d, J=7.5Hz).

MASS: 298, 280, 265, 229, 210.

Anal. Calcd. for C$_{16}$H$_{18}$N$_4$O$_2$: C 64.42, H 6.08, N 18.78 Found: C 64.48, H 6.14, N 18.71.

EXAMPLE 16

To a solution of trans-4-[N-[1-(cyanoimino)propyl]amino]-3,4-dihydro-2,2-dimethyl-3-hydroxy-2H-1-benzopyran-6-carbonitrile (1.49 g) in dry pyridine (7.5 ml) was added dropwise mesyl chloride (0.77 g) under ice-water cooling. The resulting mixture was stirred overnight at room temperature and concentrated under reduced pressure. The residue was dissolved in a mixture of ethyl acetate and washed with 5% hydrochloric acid (twice), aqueous sodium bicarbonate and brine, successively. The organic layer was dried over anhydrous magnesium sulfate and evaporated in vacuo. The residue was recrystallized from ethanol to give trans-4-[N-[1-(cyanoimino)propyl]amino]-3,4-dihydro-2,2-dimethyl-3-mesyloxy-2H-1-benzopyran-6-carbonitrile (1.50 g).

mp: 189 to 190° C. (dec.).

IR (Nujol): 3300, 2225, 2180 cm$^{-1}$.

NMR (DMSO-d$_6$, δ): 1.25 (3H, t, J=7.7Hz), 1.36 (3H, s), 1.45 (3H, s), 2.58 (2H, quartet, J=7.7Hz), 3.39 (3H, s), 4.91 (1H, d, J=5.7Hz), 5.18 (1H, t, J=6.4Hz), 7.05 (1H, d, J=8.5Hz), 7.73 (1H, dd, J=8.5 J=2.0Hz), 7.82 (1H, d, J=2.0Hz), 9.26 (1H, d, J=7.1Hz).

MASS: 280, 265.

Anal. Calcd. for C$_{17}$H$_{20}$N$_4$O$_4$S: C 54.24, H 5.36, N 14.88 Found: C 54.38, H 5.30, N 14.77.

EXAMPLE 17

The following compound was obtained according to a similar manner to that of Example 14.

4-[N-[1-(Cyanoimino)propyl]amino]-2,2-dimethyl-2H-1-benzopyran-6-carbonitrile mp: 171° to 172° C.

IR (Nujol): 2225, 2180, 1660, cm$^{-1}$.

NMR (DMSO-d$_6$, δ): 1.31 (3H, t, J=7.6Hz), 1.46 (6H, s), 2.70 (2H, quartet, J=7.6Hz), 6.10 (1H, s), 6.98 (1H, d, J=8.4Hz), 7.63 (1H, d, J=20Hz), 7.66 (1H, dd, J=8.4Hz, J=2.0Hz), 9.97 (1H, br s).

Anal. Calcd. for C: C 68.55, H 5.75, N 19.99 Found: C 68.48, H 5.87, N 19.92.

MASS: 280, 265, 238, 210.

EXAMPLE 18

The following compound was obtained according to a similar manner to that of Example 15.

trans-4-[[(Cyanoimino)(phenyl)methyl]amino]-3,4-dihydro-2,2-dimethyl-3-hydroxy-2H-1-benzopyran-6-carbonitrile mp: 147 to 150° C. (dec.).

IR (Nujol): 3470, 3430, 3235, 3075, 2230, 2180, 1610, 1095 cm$^{-1}$.

NMR (DMSO-d$_6$, δ): 1.23 (3H, s), 1.45 (3H, s), 3.77 (1H, dd, J=5.9, 9.3Hz), 5.18 (1H, br t, J=7.6Hz), 6.05 (1H, d, J=5.9Hz), 6.97 (1H, d, J=8.5Hz), 7.55–7.90 (7H, m), 9.43 (1H, d, J=7.6Hz).

MASS: 346, 328, 313, 276.

EXAMPLE 19

A solution of trans-4-amino-3,4-dihydro-2,2-dimethyl-3-hydroxy-2H-1-benzopyran-6-carbonitrile (5.0 g), methyl N-cyano-4-chlorobutyrimidate (7.36 g), triethylamine (4.8 ml), and toluene (12 ml) was stirred at 100° C. for 2 days. After being cooled to room temperature, the reaction mixture was concentrated. The residue was taken up in ethyl acetate and washed with brine, dried over anhydrous magnesium sulfate, and concentrated. After purification by column chromatography on silica gel (elution with chloroform-methanol 25:1), the crude product was further purified by recrystallization from ethyl acetate to give trans-4-(2-cyanoiminopyrrolidin-1-yl)-3,4-dihydro-2,2-dimethyl-3-hydroxy-2H-1-benzopyran-6-carbonitrile (0.87 g).

mp: 246° to 247° C.

IR (Nujol): 3350, 2230, 2180, 1600 cm$^{-1}$.

NMR (DMSO-d$_6$, δ): 1.19 (3H, s), 1.46 (3H, s), 2.0–2.2 (2H, m), 2.8–3.3 (3H, m), 3.4–3.7 (1H, m), 3.8–4.0 (1H, m), 5.16 (1H, d, J=10Hz), 5.90 (1H, d, J=5Hz), 6.97 (1H, d, J=9Hz), 7.59 (1H, br s), 7.64 (1H, br d, J=9Hz).

MASS: 292 (M+-18), 277.

Anal. Calcd. for C$_{17}$H$_{18}$N$_4$O$_2$: C 65.79, H 5.85, N 18.05 Found: C 65.65, H 5.98, N 17.88.

EXAMPLE 20

The following compounds were obtained according to a similar manner to that of Example 15.

(1) trans-4-[N-[1-(Cyanimino)butyl]amino]-3,4-dihydro-2,2-dimethyl-3-hydroxy-2H-1-benzopyran-6-carbonitrile mp: 155° to 158° C. (dec.).

IR (Nujol): 3385, 3270, 3115, 2225, 2160, 1615, 1075 cm$^{-1}$.

DMSO-d$_6$, δ): 0.99 (3H, t, J=7.4Hz), 1.19 (3H, s), 1.41 (3H, s), 1.75 (2H, septet, J=7.4Hz), 2.5–2.75 (2H, m), 3.63 (1H, dd, J=6.0, 9.2Hz), 4.97 (1H, t, J=8.4Hz), 5.82 (1H, d, J=6.02Hz), 6.96 (1H, d, J=8.5Hz), 7.52 (1H, br s), 7.64 (1H, dd, J=1.9, 8.5Hz), 9.09 (1H, d, J=7.9Hz).

MASS: 313, 294, 279.

Anal. Calcd. for C$_{17}$H$_{20}$N$_4$O$_2$: C 65.37, H 6.45, N 17.94 Found: C 65.40, H 6.52, N 17.79.

(2) trans-4-[N-(Cyanoiminomethyl)amino]-3,4-dihydro-2,2-dimethyl-3-hydroxy-2H-1-benzopyran-6-carbonitrile mp: 142° to 147° C. (dec.).

IR (Nujol): 3270, 2200, 1610 cm$^{-1}$.

NMR (DMSO-d$_6$, δ): 1.14 and 1.18 (total 3H, each s), 1.41 (3H, s), 3.62 (1H, dd, J=6.0, 9.4Hz), 4.46 (⅔H, d, J=9.4Hz), 4.96 (⅓H, d, J=9.4Hz), 5.88 (⅔H, d, J=6.0Hz), 6.06 (⅓H, d, J=6.0Hz), 6.95 (1H, d, J8.5Hz), 7.55–7.8 (2H, m), 8.45 (⅓H, br s), 8.60 (⅔H, s), 9.36 (1H, br s).

MASS: 270, 252, 237.

(3) trans-4-[N-[1-(Cyanoimino)ethyl]amino]-3,4-dihydro-2,2-dimethyl-3-hydroxy-6-mesyl-2H-1-benzopyran mp: 246° to 248° C.

IR (Nujol): 3340, 3300, 3140, 2180 cm$^{-1}$.

DMSO-d$_6$, δ): 1.19 (3H, s), 1.42 (3H, s), 2.34 (3H, s), 3.17 (3H, s), 3.60 (1H, dd, J=6, 9Hz), 5.02 (1H, t-like, J=ca. 8Hz), 5.86 (1H, d, J=6Hz), 7.01 (1H, d, J=9Hz), 7.60 (1H, d, J=2Hz), 7.73 (1H, dd, J=2, 9Hz), 9.21 (1H, d, J=8Hz).

MASS: 319 (M+-18), 304.

Anal. Calcd. for $C_{15}H_{19}N_3O_4S$: C 53.40, H 5.68, N 12.45 Found: C 53.01, H 5.68, N 12.17.

(4) trans-4-[N-[1-(Cyanoimino)ethyl]amino]-3,4-dihydro-3-hydroxy-N,N-2,2-tetramethyl-2H-1-benzopyran-6-sulfonamide mp: 220° to 221° C.

IR (Nujol): 3330, 2200 cm$^{-1}$.

NMR (DMSO-d$_6$, δ): 1.20 (3H, s), 1.43 (3H, s), 2.33 (3H, s), 2.57 (6H, s), 3.66 (1H, dd, J=4, 5Hz), 4.9-5.0 (1H, m), 5.88 (1H, d, J=5Hz), 7.00 (1H, d, J=8Hz), 7.38 (1H, d, J=2Hz), 7.54 (1H, dd, J=2, 8Hz), 9.23 (1H, d, J=8Hz).

MASS: 366, 333.

Anal. Calcd. for $C_{16}H_{22}N_4O_4S$: C 52.44, H 6.05, N 15.29 Found: C 52.19, H 6.02, N 15.03.

(5) trans-4-[N-[1-(Cyanoimino)ethyl]amino]-3,4-dihydro-3-hydroxy-2,2-dimethyl-6-nitro-2H-1-benzopyran mp: 155° to 157° C.

IR (Nujol): 3570, 3400, 3230, 3080, 2200, 1520 cm$^{-1}$.

NMR [DMSO-d$_6$, δ) 1.22 (3H, s), 1.45 (3H, s), 2.37 (3H, s), 3.67 (1H, dd, J=5, 8Hz), 5.02 (1H, br t, J=8Hz), 5.94 (1H, d, J=5Hz), 7.01 (1H, d, J=9Hz), 7.97 (1H, d, J=3Hz), 8.09 (1H, dd, J=3, 9Hz), 9.26 (1H, br d, J=8Hz).

MASS: 304, 286, 271.

(6) trans-6-Acetyl-4-[N-[1-(cyanoimino)ethyl]amino]-3,4-dihydro-3-hydroxy-2,2-dimethyl-2H-1-benzopyran mp: 199° to 201° C.

IR (Nujol): 3420, 3300, 3130, 2190, 1660 cm$^{-1}$.

NMR (DMSO-d$_6$, δ): 1.18 (3H, s), 1.41 (3H, s), 2.35 (3H, s), 2.50 (3H, s), 3.61 (1H, dd, J=6, 9Hz), 5.00 (1H, t, J=9Hz), 5.80 (1H, d, J=6Hz), 6.89 (1H, d, J=9Hz), 7.67 (1H, br s), 7.82 (1H, dd, J=2, 9Hz), 9.18 (1H, d, J=9Hz).

MASS: 301, 283, 268.

Anal. Calcd. for $C_{16}H_{19}N_3O_3$: C 63.77, H 6.35, N 13.94 Found: C 63.64, H 6.39, N 13.68.

(7) trans-6-Bromo-4-[N-[1-(cyanoimino)ethyl]amino]-3,4-dihydro-3-hydroxy-2,2-dimethyl-2H-1-benzopyran mp: 252 to 254° C. (dec.).

IR (Nujol): 3475, 3220, 3080, 2175, 1085 cm$^{-1}$.

NMR (DMSO-d$_6$, δ): 1.13 (3H, s), 1.36 (3H, s), 2.31 (3H, s), 3.54 (1H, dd, J=6, 9Hz), 4.94 (1H, t, J=9Hz), 5.68 (1H, d, J=6Hz), 6.72 (1H, t, J=8Hz), 7.18 (1H, d, J=2Hz), 7.31 (1H, dd, J=2, 8Hz), 9.08 (1H, d, J=9Hz).

MASS: 337, 339, 319, 321, 304, 306.

Anal. Calcd. for $C_{14}H_{16}BrN_3O_2$: C 49.72, H 4.77, N 12.42 Found: C 49.32, H 4.81, N 11.86.

EXAMPLE 21

The following compounds were obtained according to a similar manner to that of Example 16.

(1) trans-4-[[(Cyanoimino)(phenyl)methyl]amino]-3,4-dihydro-2,2-dimethyl-3-mesyloxy-2H-1-benzopyran-6-carbonitrile mp: 216° to 217° C. (dec.).

IR (Nujol): 3290, 2220, 2175, 1608, 1340 cm$^{-1}$.

NMR (DMSO-d$_6$, δ): 1.39 (3H, s), 1.50 (3H, s), 3.41 (3H, s), 5.07 (1H, d, J=6.1Hz), 5.41 (1H, br t, J=6.5Hz), 7.05 (1H, d, J=8.6Hz), 7.50-7.85 (6H, m), 7.97 (1H, br s), 9.68 (1H, d, J=7.2Hz).

MASS: 217.

Anal Calcd. for $C_{21}H_{20}N_4O_4S$: C 59.42, H 4.75, N 13.20, S 7.55 Found: C 59.49, H 4.75, N 12.91, S 7.80.

(2) trans-4-[N-[1-(Cyanoimino)butyl]amino]-3,4-dihydro-2,2-dimethyl-3-mesyloxy-2H-1-benzopyran-6-carbonitrile mp: 179° to 181° C.

IR (Nujol): 3245, 3100, 2230, 2180 cm$^{-1}$.

NMR (DMSO-d$_6$, δ): 0.97 (3H, t, J=7.4Hz), 1.37 (3H, s), 1.43 (3H, s), 1.73 (2H, septet, J=7.4Hz), 2.45-2.65 (2H, m), 3.40 (3H, s), 4.91 (1H, d, J=5.2Hz), 5.16 (1H, t, J=6.0Hz), 7.06 (1H, d, J=8.5Hz), 7.74 (1H, dd, J=2.0, 8.5Hz), 7.78 (1H, br s), 9.30 (1H, d, J=6.8Hz).

MASS: 390, 294, 279.

Anal. Calcd. for $C_{18}H_{22}N_4O_4S$: C 55.37, H 5.68, N 14.35 Found: C 55.65, H 5.69, N 14.21.

(3) trans-4-(2-Cyanoiminopyrrolidin-1-yl)-3,4-dihydro-2,2-dimethyl-3-mesyloxy-2H-1-benzopyran-6-carbonitrile mp: 243° to 245° C.

IR (Nujol): 2220, 2180, 1580 cm$^{-1}$.

NMR (DMSO-d$_6$, δ): 1.28 (3H, s), 1.55 (3H, s), 1.9-2.2 (2H, m), 2.7-3.3 (3H, m), 3.33 (3H, s), 3.4-3.7 (1H, m), 5.0-5.2 (1H, m), 5.5-5.7 (1H, m), 7.06 (1H, d, J=8Hz), 7.72 (1H, br d, J=8Hz), 7.77 (1H, br s).

MASS: 309 (M$^+$-79), 292, 277.

EXAMPLE 22

The following compounds were obtained according to a similar manner to that of Example 14.

(1) 4-[[(Cyanoimino)(phenyl)methyl]amino]-2,2-dimethyl-2H-1-benzopyran-6-carbonitrile mp: 256° to 259° C. (dec.).

IR (Nujol): 3330, 3155, 2220, 2175, 1655, 1610 cm$^{-1}$.

NMR (DMSO-d$_6$, δ): 1.49 (6H, s), 6.17 (1H, s), 7.01 (1H, d, J=8.9Hz), 7.6-8.0 (8H, m)

MASS: 328, 313.

Anal. Calcd. for $C_{20}H_{16}N_4O$: C 73.15, H 4.91, N 17.06 Found: C 72.80, H 4.86, N 16.61.

(2) 4-[N-[1-(Cyanoimino)butyl]amino]-2,2-dimethyl-2H-1-benzopyran-6-carbonitrile mp: 131° to 133° C.

IR (Nujol): 3180, 3050, 2225, 2170, 1665, 1600.

NMR (DMSO-d$_6$, δ): 1.02 (3H, t, J=7.4Hz), 1.46 (6H, s), 1.79 (2H, septet, J=7.4Hz), 2.68 (2H, t, J=7.4Hz), 6.08 (1H, s), 6.99 (1H, d, J=8.4Hz), 7.60 (1H, d, J=2.0Hz), 7.67 (1H, dd, J=2.0, 8.4Hz), 9.97 (1H, br s).

MASS: 294, 279.

Anal. Calcd for $C_{17}H_{18}N_4O$: C 69.37, H 6.16, N 19.03 Found: C 69.36, H 6.29, N 18.96.

(3) 4-(2-Cyanoiminopyrrolidin-1-yl)-2,2-dimethyl-2H-1-benzopyran-6-carbonitrile mp: 267° to 269° C.

IR (Nujol): 2220, 2180, 1660, 1600 cm$^{-1}$.

NMR (DMSO-d$_6$, δ): 1.46 (6H, s), 2.1-2.3 (2H, m), 3.03 (2H, t-like, J=ca. 8Hz), 3.81 (2H, t, J=7Hz), 6.09 (1H, s), 6.99 (1H, d, J=8Hz), 7.6-7.7 (2H, m).

MASS 292, 277.

Anal. Calcd. for $C_{17}H_{16}N_4O$: C 69.85, H 5.52, N 19.16 Found: C 69.72, H 5.64, N 18.83.

EXAMPLE 23

To a solution of trans-4-[N-(cyanoiminomethyl)amino]-3,4-dihydro-2,2-dimethyl-3-hydroxy-2H-1-benzopyran-6-carbonitrile (1.08 g) in dry pyridine (5.4 ml) was added mesyl chloride (0.77 ml) under ice-water cooling. The reaction mixture was stirred for 2 hours and 20 minutes at ambient temperature and evaporated. The residue was suspended in toluene (26 ml) and thereto was added 1,8-diazabicyclo[5,4,0]undec-7-ene (0.89 ml). The reaction mixture was stirred at 70° C. for 50 minutes and concentrated under reduced pressure. The residue was dissolved in ethyl acetate and then washed with brine. The organic layer was dried over anhydrous magnesium sulfate and concentrated under reduced pressure. The residue was subjected to a column chromatography on silica gel (28 g) and eluted with a mixture of ethyl acetate and n-hexane (1:4→1:1). The fractions containing the object compound were combined and concentrated under reduced pressure. The residue was recrystallized from 50% aqueous ethanol to give 4-[N-(cyanoiminomethyl)amino]-2,2-dimethyl-2H-1-benzopyran-6-carbonitrile (0.38 g).

mp: 159° to 161° C.

IR (Nujol): 2115, 1665, 1635 cm$^{-1}$.

NMR (DMSO-d$_6$, δ): 1.45 (3H, s), 1.46 (3H, s), 5.97 (½H, s), 6.34 (½H, s), 7.00 (1H, d, J=8.4Hz), 7.6-7.8 (2H, m), 8.53 (½H, s), 8.73 (½H, br s), 10.60 (1H, br s).

MASS: 252, 237.

EXAMPLE 24

The following compound was obtained according to a similar manner to that of Example 1.

trans-2,2-Dimethyl-4-(1,1-dioxo-1,2,5-thiadiazolidin-2--yl)-3-hydroxy-2H-1-benzopyran-6-carbonitrile mp: 180° to 183° C.

IR (Nujol): 3560, 3245, 2225, 1162 cm$^1$.

NMR (DMSO-d$_6$, δ): 1.18 (3H, s), 1.46 (3H, s), 2.87-3.80 (5H, m), 4.41 (1H, d, J=10Hz), 5.66 (1H, br s), 6.90 (1H, d, J=8Hz), 7.14 (1H, br s), 7.59 (1H, dd, J=2, 8Hz), 7.77 (1H, d, J=2Hz).

MASS: 323, 290, 252.

Anal. Calcd. for C$_{14}$H$_{17}$N$_3$O$_4$S: C 52.00, H 5.30, N 12.99 Found: C 52.09, H 5.29, N 12.86.

EXAMPLE 25

To a solution of 1,1-dioxo-2-methyl-1,2,5-thiadiazolidine (0.89 g) in dimethyl sulfoxide 22 ml) was added 60% sodium hydride (0.26 g) in mineral oil portionwise under water-cooling. The reaction mixture was stirred at ambient temperature for 30 minutes and thereto was added 3,4-dihydro-2,2-dimethyl-3,4-epoxy-2H-1-benzopyran-6-carbonitrile (0.88 g). The reaction mixture was stirred at ambient temperature for 2 days, poured into ice-water (65 g), extracted with ethyl acetate. The extract was washed with brine, dried over anhydrous magnesium sulfate, and evaporated in vacuo. The residue was subjected to column chromatography on silica gel (45 g) and eluted with a mixture of methanol and chloroform (1:50). The fractions containing object compound were combined and concentrated under reduced pressure. The residue was recrystallized from ethanol to give white crystal of trans-2,2-dimethyl-4-[1,1-dioxo-5-methyl-1,2,5-thiadiazolidin-2-yl)-3-hydroxy-2H-1-benzopyran-6-carbonitrile (0.28 g).

mp: 213° to 214° C.

IR (Nujol): 3520, 2220, 1607, 1275 cm$^{-1}$.

NMR (DMSO-d$_6$, δ): 1.17 (3H, s), 1.43 (3H, s), 2.67 (3H, s), 2.83-3.50 (4H, m), 3.64 (1H, dd, J=6, 10Hz), 4.44 (1H, d, J=10Hz), 5.80 (1H, d, J=6Hz), 6.92 (1H, d J=8Hz), 7.61 (1H, dd, J=2, 8Hz), 7.70 (1H, d, J=2Hz).

MASS: 337, 304, 266.

Anal. Calcd. for C$_{15}$H$_{19}$N$_3$O$_4$S:

C 53.40, H 5.68, N 12.45 Found: C 52.91, H 5.57, N 12.35.

EXAMPLE 26

The following compounds were obtained according to a similar manner to that of Example 2.

(1) 4-[N-[1-(Cyanoimino)ethyl]amino]-2,2-dimethyl-6-mesyl-2H-1-benzopyran mp: 181° to 182° C.

IR(Nujol): 3240, 3070, 2180, 1670 cm$^{-1}$.

NMR(DMSO-d$_6$, δ): 1.46 (6H, s), 2.44 (3H, s), 3.18 (3H, s), 6.12 (1H, s), 7.04 (1H, d, J=8Hz), 7.66 (1H, d, J=2Hz), 7.74 (1H, dd, J=2, 8Hz), 10.12 (1H, br s).

MASS: 319, 304.

Anal. Calcd. for C$_{15}$H$_{17}$N$_3$O$_3$S: C 56.41, H 5.36, N 13.16 Found: C 56.16, H 5.36, N 12.90.

(2) 4-[N-[1-(Cyanoimino)ethyl]amino]-2,2-dimethyl-6-nitro-2H-1-benzopyran mp: 200° to 201° C.

IR (Nujol): 3200, 3050, 2170, 1660 cm$^{-1}$.

NMR (DMS 6): 1.54 (6H, s), 2.58 (3H, s), 6.38 (1H, s), 6.91 (1H, d, J=10Hz), 7.65 (1H, br s), 8.0-8.1 (2H, m).

MASS: 286, 271, 256.

Anal. Calcd. for C$_{14}$H$_{14}$N$_4$O$_3$: C 58.74, H 4.93, N 19.57 Found: C 59.01, H 5.00, N 19.53.

(3) 2,2-Dimethyl-4-(1,1-dioxo-5-methyl-1,2,5-thiadiazolidin-2-yl)-2H-1-benzopyran-6-carbonitrile mp: 147° to 148° C.

IR (Nujol): 2225, 1637, 1328 cm$^{-1}$.

NMR (CDCl$_3$, δ): 1.50 (6H, s), 2.83 (3H, s), 3.32-3.74 (4H, m), 6.00 (1H, s), 6.83 (1H, d, J=8Hz), 7.42 (1H, dd, J=2, 8Hz), 7.61 (1H, d, J=2Hz).

MASS 319, 304.

Anal. Calcd. for C$_{15}$H$_{17}$N$_3$O$_3$S: C 56.41, H 5.36, N 13.16 Found: C 56.13, H 5.31, N 13.10.

EXAMPLE 27

The following compounds were obtained according to a similar manner to that of Example 23.

(1) 6-Bromo-4-[N-[1-(cyanoimino)ethyl]amino]-2,2-dimethyl-2H-1-benzopyran mp: 167° to 169° C. (dec.).

IR (Nujol): 3185, 2180, 1645 cm$^{-1}$.

NMR (DMSO-d$_6$, δ): 1.41 (6H, s), 2.42 (3H, s); 6.03 (1H, s), 6.79 (1H, d, J=9.2Hz), 7.3-7.4 (2H, m), 9.97 (1H, br s).

MASS: 319, 321, 304, 306.

(2) 4-[N-[1-(Cyanoimino)ethyl]amino]-N,N,2,2-tetramethyl-2H-1-benzopyran-6-sulfonamide mp: 213° to 214° C.

IR (Nujol): 3220, 3050, 2180, 1670 cm$^{-1}$.

NMR (DMSO-d$_6$, δ): 1.47 (6H, s), 2.43 (3H, s), 2.59 (6H, s), 6.03 (1H, s), 7.03 (1H, d, J=9Hz), 7.37 (1H, d, J=2Hz), 7.54 (1H, dd, J=2, 9Hz), 10.23 (1H, br s).

MASS: 348, 333.

Anal. Calcd. for C$_{16}$H$_{20}$N$_4$O$_3$S: C 55.16, H 5.79, N 16.08 Found: C 55.12, H 5.65, N 16.01.

EXAMPLE 28

The following compound was obtained according to a similar manner to that of Example 1.

trans-4-(2-Cyanoiminothiazolidin-3-yl}-3,4-dihydro-3-hydroxy-2,2,6-trimethyl-2H-1-benzopyran mp: 234° to 235° C.

IR (Nujol): 3290, 2190, 1570 cm$^{-1}$.

NMR (DMSO-d$_6$, δ): 1.12 (3H, s), 1.41 (3H, s), 2.22 (3H, s), 3.3-3.6 (3H, m), 3.65-3.9 (2H, m), 5.17 (1H, d, J=10.0Hz), 5.83 (1H, d, J=5.7Hz), 6.65-6.75 (2H, m), 7.00 (1H, br d, J=8.3Hz).

MASS: 317, 299, 284.

Anal. Calcd. for $C_{16}H_{19}N_3O_2S$: C 60.55, H 6.03, N 13.24 Found: C 60.55, H 6.14, N 13.06.

EXAMPLE 29

The following compounds were obtained according to a similar manner to that of Example 15.

(1) trans-4-[N-[1-(Cyanoimino)ethyl]amino]-3,4-dihydro-3-hydroxy-2,2,6-trimethyl-2H-1-benzopyran mp: 243° to 245° C.

IR (Nujol): 3500, 3240, 3100, 2175 cm$^{-1}$.

NMR(DMSO-d$_6$, δ): 1.12 (3H, s), 1.36 (3H, s), 2.20 (3H, s), 2.32 (3H, s), 3.52 (1H, dd, J=9.3, 5.5Hz), 4.94 (1H, t, J=9.0Hz), 5.62 (1H, d, J=5.5Hz), 6.65 (1H, d, J=8.2Hz), 6.87 (1H, br s), 6.96 (1H, d, J=8.2Hz), 9.10 (1H, d, J=8.7Hz).

MASS: 273, 255, 240.

(2) 4-[N-[1-(Cyanoimino)ethyl]-N-methylamino]-3,4-dihydro-3-hydroxy-2,2-dimethyl-2H-1-benzopyran-6-carbonitrile mp: 258° to 259° C.

IR (Nujol): 3325, 3280, 2225, 2190, 1560 cm$^{-1}$.

(DMSO-d$_6$, δ): 1.19, 1.21 (total 3H, each s), 1.45, 1.47 (total 3H, each s), 2.52 (1.8H, s), 2.58 (1.2H, s), 2.62 (1.2H, s), 2.80 (1.8H, s), 3.7–3.8 (1H, m), 4.98 (0.4H, d, J=9.6Hz), 5.7–5.9 (1H, m), 6.14 (0.4H, d, J=5.9Hz), 6.9–7.1 (1H, m), 7.5–7.7 (2H, m).

MASS: 298, 280, 265, 221, 56.

Anal. Calcd. for $C_{16}H_{18}N_4O_2$: C 64.42, H 6.08, N 18.78. Found: C 64.38, H 6.22, N 18.40.

(3) Ethyl trans-4-[N-[1-(cyanoimino)ethyl]amino]-3,4-dihydro-3-hydroxy-2,2-dimethyl-2H-1-benzopyran-6-carboxylate mp: 194° to 196° C.

IR (Nujol): 3300, 2190, 1685, 1580 cm$^{-1}$.

NMR (DMSO-d$_6$, δ): 1.18 (3H, s), 1.29 (3H, t, J=7.1Hz), 1.41 (3H, s), 2.35 (3H, s), 3.61 (1H, dd, J=9.1, 5.5Hz), 4.27 (2H, quartet, J=7.1Hz), 4.99 (1H, t, J=8.7Hz), 5.81 (1H, d, J=5.5Hz), 6.88 (1H, d, J=8.6Hz), 7.68 (1H, br s), 7.77 (1H, dd, J=8.6, 2.0Hz), 9.19 (1H, d, J=8.4Hz).

(4) trans-4-[N-[1-(Cyanoimino)-2-methylpropyl]amino]-3,4-dihydro-2,2-dimethyl-3-hydroxy-2H-1-benzopyran-6-carbonitrile mp: 215° to 216.5° C.

IR (Nujol): 3225, 3090, 2225, 2190, 1610, 1565 cm$^{-1}$.

NMR (DMSO-d$_6$, δ): 1.19 (3H, s), 1.31 (3H, d, J=7.0Hz), 1.32 (3H, d, J=7.0Hz), 1.42 (3H, s), 3.09 (1H, septet, J=7.0Hz), 3.74 (1H, dd, J=9.3, 6.0Hz), 5.01 (1H, br t, J=8.7Hz), 5.84 (1H, d, J=6.0Hz), 6.97 (1H, d, J=8.5Hz), 7.43 (1H, br s), 7.65 (1H, dd, J=8.5, 1.9Hz), 8.70 (1H, d, J=8.2Hz).

Anal. Calcd. for $C_{17}H_{20}N_4O_2$: C 65.37, H 6.45, N 17.94 Found: C 64.90, H 6.74, N 17.50.

EXAMPLE 30

The following compound was obtained according to a similar manner to that of Example 16.

trans-4-[N-[1-(Cyanoimino)-2-methylpropyl]amino]-3,4-dihydro-2,2-dimethyl-3-mesyloxy-2H-1-benzopyran-6-carbonitrile mp 210° to 211° C.

IR (Nujol): 3240, 3100, 2225, 2180, 1610, 1550 cm$^{-1}$.

NMR (DMSO-d$_6$, δ): 1.29 (3H, d, J=7.0Hz), 1.30 (3H, d, J=7.0Hz), 1.34 (3H, s), 1.47 (3H, s), 3.05 (1H, septet, J=7.0Hz), 3.37 (3H, s), 4.98 (1H, d, J=6.2Hz), 5.22 (1H, br t, J=6.5Hz), 7.06 (1H, d, J=8.2Hz), 7.65–7.8 (2H, m), 8.93 (1H, d, J=7.1Hz).

MASS: 390, 311, 294, 279.

Anal Calcd. for $C_{18}H_{22}N_4O_4S$: C 55.37, H 5.68, N 14.35 Found: C 55.54, H 5.80, N 14.14.

EXAMPLE 31

The following compound was obtained according to a similar manner to that of Example 2.

4-(2-Cyanoiminothiazolidin-3-yl)-2,2,6-trimethyl-2H-1-benzopyran mp: 107° to 108° C.

IR (Nujol): 2170, 1650, 1550 cm$^{-1}$.

NMR (DMSO-d$_6$, δ): 1.39 (6H, s), 2.23 (3H, s), 3.69 (2H, t, J=7.4Hz), 4.14 (2H, t, J=7.4Hz), 5.98 (1H, s), 6.73 (1H, d, J=8.1Hz), 6.80 (1H, d, J=1.7Hz), 7.00 (1H, dd, J=8.1, 1.7Hz).

MASS: 299, 284.

EXAMPLE 32

The following compound was obtained according to a similar manner to that of Example 14.

4-[N-[1-(Cyanoimino)-2-methylpropyl]amino]-2,2-dimethyl-2H-1-benzopyran-6-carbonitrile mp: 159° to 160° C.

IR (Nujol): 3180, 3050, 2225, 2175, 1665, 1560, 1530 cm$^{-1}$.

NMR (DMSO-d$_6$, δ): 1.36 (6H, d, J=6.9Hz), 1.47 (6H, s), 3.11 (1H, septet, J=6.9Hz), 6.00 (1H, s), 6.99 (1H, d, J=8.4Hz), 7.41 (1H, d, J=1.9Hz), 7.66 (1H, dd, J=8.4, 1.9Hz), 9.75 (1H, s).

MASS: 294, 279.

Anal. Calcd. for $C_{17}H_{18}N_4O$: C 69.37, H 6.16, N 19.03 Found: C 69.43, H 6.15, N 19.02.

EXAMPLE 33

A mixture of ethyl 4-(2-cyanoiminothiazolidin-3-yl)-2,2-dimethyl-2H-1-benzopyran-6-carboxylate (1.15 g) and lithium iodide (3.44 g) in 2,6-lutidine (11.5 ml) was refluxed overnight. The resulting mixture was dissolved in a mixture of ethyl acetate and 10% hydrochloric acid, and the organic layer was separated and washed with brine. The extract was dried over anhydrous magnesium sulfate and concentrated in vacuo. The residue was purified by column chromatography on silica gel (elution with 30:1 to 4:1 chloroform-methanol) followed by recrystallization from ethanol to give 4-(2-cyanoiminothiazolidin-3-yl)-2,2-dimethyl-2H-1-benzopyran-6-carboxylic acid (0.63 g).

mp: 238° to 239° C. (dec.).

IR (Nujol): 3320, 2630, 2190, 1710, 1685, 1660, 1610, 1550 cm$^{-1}$.

NMR (DMSO-d$_6$, δ): 1.45 (6H, s), 3.70 (2H, t, J=7.5Hz), 4.20 (2H, t, J=7.5Hz), 6.14 (1H, s), 6.92 (1H, d, J=8.4Hz), 7.46 (1H, d, J=2.0Hz), 7.79 (1H, dd, J=8.4, 2.0Hz), 12.9 (1H, br s).

MASS: 329, 314, 296.

What we claim is:

1. A compound of the formula:

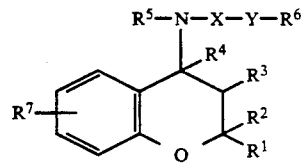

wherein $R^1$ and $R^2$ are each lower alkyl, $R^3$ is hydroxy or acyloxy derived from an acid selected from the group consisting of carboxylic, carbonic, carbamic and sulfonic acid, and $R^4$ is hydrogen, or $R^3$ and $R^4$ are linked together to form a bond, $R^5$ is hydrogen and $R^6$ is lower alkyl, or $R^5$ and $R^6$ are linked together to form lower alkylene, $R^7$ is lower alkylsulfonyl or N,N-di(lower)alkylsulfamoyl, X is cyanoiminomethylene, and Y is thio or imino which may be substituted with lower alkyl, or pharmaceutically acceptable salt thereof.

2. A compound of claim 1, in which
$R^3$ is hydroxy, lower alkanoyloxy or lower alkylsulfonyloxy and $R^4$ is hydrogen, or
$R^3$ and $R^4$ are linked together to form a bond.

3. A compound of claim 2, in which
$R^3$ is hydroxy and $R^4$ is hydrogen, or
$R^3$ and $R^4$ are linked together to form a bond,
$R^5$ and $R^6$ are linked together to form ethylene, and
Y is thio.

4. A compound of claim 3, which is selected from the group consisting of:
trans-4-(2-cyanoiminothiazolidin-3-yl)-3,4-dihydro-3-hydroxy-6-mesyl-2,2-dimethyl-2H-1-benzopyran, and
4-(2-cyanoiminothiazolidin-3-yl)-6-mesyl-2,2-dimethyl-2H-1-benzopyran.

5. A pharmaceutical composition which comprises, as an active ingredient, an effective amount of a compound of claim 2 or a pharmaceutically acceptable salt thereof in admixture with a pharmaceutically acceptable carrier.

6. A method for the treatment of $K^+$ channel diseases which comprises administering an effective amount of a compound of claim 1 or a pharmaceutically acceptable salt thereof to a human or animal.

7. A method for the treatment of hypertension which comprises administering an effective amount of a compound of claim 1 or a pharmaceutically acceptable salt thereof to a human or animal.

* * * * *